United States Patent
Stoffers et al.

(10) Patent No.: US 10,987,407 B2
(45) Date of Patent: *Apr. 27, 2021

(54) METHODS AND COMPOSITIONS FOR TREATING HYPOGLYCEMIC DISORDERS

(71) Applicants: THE TRUSTEES OF THE UNIVERSITY OF PENNSYLVANIA, Philadelphia, PA (US); THE CHILDREN'S HOSPITAL OF PHILADELPHIA, Philadelphia, PA (US)

(72) Inventors: Doris Stoffers, Moorestown, NJ (US); Diva D. De Leon, Penn Valley, PA (US); Charles Stanley, Drexel Hill, PA (US)

(73) Assignees: THE TRUSTEES OF THE UNIVERSITY OF PENNSYLVANIA, Philadelphia, PA (US); CHILDREN'S HOSPITAL OF PHILADELPHIA, Philadelphia, PA (US)

(*) Notice: Subject to any disclaimer, the term of this patent is extended or adjusted under 35 U.S.C. 154(b) by 67 days.

This patent is subject to a terminal disclaimer.

(21) Appl. No.: 16/258,686

(22) Filed: Jan. 28, 2019

(65) Prior Publication Data

US 2019/0336584 A1 Nov. 7, 2019

Related U.S. Application Data

(63) Continuation of application No. 15/453,823, filed on Mar. 8, 2017, now Pat. No. 10,188,702, which is a continuation of application No. 12/081,123, filed on Apr. 10, 2008, now Pat. No. 9,616,108, which is a continuation-in-part of application No. PCT/US2008/000281, filed on Jan. 8, 2008.

(60) Provisional application No. 60/879,033, filed on Jan. 8, 2007.

(51) Int. Cl.
*A61K 38/26* (2006.01)

(52) U.S. Cl.
CPC .................................. *A61K 38/26* (2013.01)

(58) Field of Classification Search
None
See application file for complete search history.

(56) References Cited

U.S. PATENT DOCUMENTS

| 5,424,286 | A | 6/1995 | Eng |
| 6,469,021 | B1 | 10/2002 | Truesdale et al. |
| 6,573,291 | B2 | 6/2003 | Gronberg et al. |
| 6,903,074 | B1 | 6/2005 | Morgan et al. |
| 8,268,781 | B2 | 9/2012 | Gotthardt et al. |
| 9,616,108 | B2 * | 4/2017 | Stoffers .................. A61K 38/26 |
| 9,821,031 | B2 | 11/2017 | Stoffers et al. |
| 10,188,702 | B2 * | 1/2019 | Stoffers .................. A61K 38/26 |
| 2002/0123461 | A1 | 9/2002 | Drucker et al. |
| 2004/0092443 | A1 | 5/2004 | Fridkin et al. |
| 2004/0116331 | A1 | 6/2004 | Seeley et al. |
| 2008/0269130 | A1 | 10/2008 | Stoffers et al. |
| 2010/0029554 | A1 | 2/2010 | Ghosh et al. |
| 2011/0124555 | A1 | 5/2011 | Schmid |
| 2015/0274800 | A1 | 10/2015 | Schellenberger et al. |
| 2015/0368311 | A1 | 12/2015 | Haack et al. |
| 2018/0117122 | A1 | 5/2018 | McLaughlin et al. |
| 2018/0147261 | A1 | 5/2018 | McLaughlin et al. |
| 2019/0336584 | A1 | 11/2019 | Stoffers et al. |

FOREIGN PATENT DOCUMENTS

| WO | WO 02/081649 | 10/2002 |
| WO | 2008-085982 A2 | 7/2008 |
| WO | 2016-191394 A1 | 12/2016 |
| WO | 2016-191395 A1 | 12/2016 |
| WO | 2018-094404 A1 | 5/2018 |

OTHER PUBLICATIONS

Stanley et al. ('Editorial: Advances in diagnosis and treatment of hyperinsulinism in infants and children' The Journal of Endocrinology & Metabolism v87(11) 2002 pp. 4857-4859) (Year: 2002).*
Song J et al, "NMR for the design of functional mimetics of protein-protein interactions: one key is in the building of bridges." Biochem Cell Biol 76(2-3) 177-188, 1998.
Vogt A et al, "A non-peptide mimetic of Ras-CAAX: selective inhibition of farnesyltransferase and Ras processing." J Biol Chem. 270(2): 660-4, 1995.
Alexopoulos K et al, "Design and synthesis of novel biologically active thrombin receptor non-peptide mimetics based on the pharmacophoric cluster Phe/Arg/NH2 of the Ser42-Phe-Leu-Leu-Arg46 motif sequence: platelet aggregation and relaxant activities." J Med Chem 47(13): 3338-52, 2004.
Andronati SA et al, "Peptidomimetics—antagonists of the fibrinogen receptors: molecular design, structures, properties and therapeutic applications." Curr Med Chem 11(9): 1183-211, 2004.
Breslin MJ et al, "Non-peptide alphavbeta3 antagonists. Part 6: design and synthesis of alphavbeta3 antagonists containing a pyridone or pyrazinone central scaffold." Bioorg Med Chem Lett 13(10): 1809-12, 2003.
Caudy AA et al, "Fragile X-related protein and VIG associate with the RNA interference machinery." Genes & Devel 16: 2491-96, Oct. 2002.
Neilsen PE, Current Opinion in Structural Biology 9:353-57; 1999.
Naz RK et al. Novel human prostate-specific cDNA: molecular cloning, expression, and immunobiology of the recombinant protein. 2002 Biochem Biophys Res Commun. 297:1075-84.

(Continued)

*Primary Examiner* — Ronald T Niebauer
(74) *Attorney, Agent, or Firm* — Mark S. Cohen; Pearl Cohen; Zedek Latzer Baratz LLP

(57) ABSTRACT

This invention relates to methods of treating and ameliorating congenital and neonatal hyperinsulinism and post-prandial hypoglycemia, comprising the step of administering an antagonist of the Glucagon-Like Peptide-1 (GLP-1) receptor, e.g. a GLP-1 fragment or analogue thereof.

11 Claims, 11 Drawing Sheets

Specification includes a Sequence Listing.

(56) References Cited

OTHER PUBLICATIONS

Field et al., "Purification of a RAS-responsive adenylyl cyclase complex from *Saccharomyces cerevisiae* by use of an epitope addition method." Mol. Cell. Biol., 8: 2159; May 1998.
Evan et al., "Isolation of monoclonal antibodies specific for human c-myc proto-oncogene product." Molecular and Cellular Biology, 5: 3610; Dec. 1985.
Paborsky et al., "Mammalian cell transient expression of tissue factor for the production of antigen." Protein Engineering, 3(6): 547; 1990.
Hopp et al., A Short Polypeptide Marker Sequence Useful for Recombinant Protein Identification and Purification. BioTechnology, 6: 1204-1210 (1988)).
Martin et al., "GAP domains responsible for ras p21-dependent inhibition of muscarinic atrial K+ channel currents." Science, 255: 192; Jan. 10, 1992.
Skinner et al., "Use of the Glu-Glu-Phe C-terminal epitope for rapid purification of the catalytic domain of normal and mutant ras GTPase-activating proteins." J. Biol. Chem., 266:14163-14166, 1991.
Lutz-Freyermuth et al., "Quantitative determination that one of two potential RNA-binding domains of the A protein component of the U1 small nuclear ribonucleoprotein complex binds with high affinity to stem-loop II of U1 RNA ." Proc. Natl. Acad. Sci. USA, 87: 6393-6397 (1990).
LaRochelle et al., "Specific receptor detection by a functional keratinocyte growth factor-immunoglobulin chimera." J. Cell Biol., 139(2): 357-66, 1995.
Heidaran et al., "Beta PDGFR-IgG chimera demonstrates that human beta PDGFR Ig-like domains 1 to 3 are sufficient for high affinity PDGF BB binding." FASEB J., 9(1): 140-5, 1995.
Ashkenazi et al.,"Immunoadhesins." Int. Rev. Immunol., 10(2-3); 2 1 9-2 7, 1993.
Cheon et al., "High-affinity binding sites for related fibroblast growth factor ligands reside within different receptor immunoglobulin-like domains." PNAS USA, 91(3): 989-93, 1994.
Miholic, J., et al., Emptying of the gastric substitute, glucagon-like peptide-1 (GLP-1), and reactive hypoglycemia after total gastrectomy. Dig Dis Sci, 1991. 36(10): p. 1361-1370.
Vilsboll, T., et al., No reactive hypoglycaemia in Type 2 diabetic patients after subcutaneous administration of GLP-1 and intravenous glucose. Diabet Med, 2001. 18(2): p. 144-149.
Todd, J.F., et al., A tumor that secretes glucagon-like peptide-1 and somatostatin in a patient with reactive hypoglycemia and diabetes. The Lancet, 2003. 361: p. 228-230.
Andreasen, J.J., C. Orskov, and J.J. Hoist, Secretion of glucagon-like peptide-1 and reactive hypoglycemia after partial gastrectomy. Digestion, 1994. 55(4): p. 221-228.
Gebhard, B., et al., Postprandial GLP-1, norepinephrine, and reactive hypoglycemia in dumping syndrome. Dig Dis Sci, 2001. 46(9): p. 1915-1923.
Toft-Nielsen, M.B., et al., Determinants of the effectiveness of glucagon-like peptide-1 in type 2 diabetes. J Clin Endocrinol Metab, 2001. 86(8): p. 3853-3860.
Edwards, C.M., et al., Subcutaneous glucagon-like peptide-1 (7-36) amide is insulinotropic and can cause hypoglycaemia in fasted healthy subjects. Clin Sci (Lond), 1998. 95(6): p. 719-724.
Eng, J., et al., (1992) Isolation and characterization of exendin-4, an exendin-3 analogue, from heloderma suspectum venom. Further evidence for an exendin receptor on dispersed acini from guinea pig pancreas. J Biol Chem, 267: p. 7402-7405.
Schirra J, Sturm K, Leicht P, Arnold R, Goke B, Katschinski M. Exendin(9-39)amide is an antagonist of glucagon-like peptide-1(7-36)amide in humans. J Clin Invest. Apr. 1, 1998;101(7):1421-30.
Schirra J, Nicolaus M, Roggel R, Katschinski M, Storr M, Woerle HJ, Goke B. Endogenous glucagon-like peptide 1 controls endocrine pancreatic secretion and antro-pyloro-duodenal motility in humans. Gut. Feb. 2006;55(2):243-51. Epub Jun. 28, 2005.
De Leon DD, Deng S, Madani R, Ahima RS, Drucker DJ, Stoffers DA. Role of endogenous glucagon-like peptide-1 in islet regeneration after partial pancreatectomy. Diabetes. Feb. 2003;52(2):365-71.
Kulkarni et al., (1995) Use of Exendin(9-39)Amide to define the in-vivo and in-vitro roles of GLP-1(7-36)Amide in the regulation of Insulin secretion. Regulatory Peptides v57(2): 201.
Cancelas J, García-Martínez JA, Villanueva-Peñacarrillo ML, Valverde I, Malaisse WJ. (2002) Resistance of succinic acid dimethyl ester insulinotropic action to exendin (9-39) amide. Horm Metab Res. Jan.;34(1):13-5.
Koh et al. "Neonatal hypoglycaemia—the controversy regarding definition" Archives of Disease in Childhood, 63, 1386-1398, (1988).
Cancelas et al. "Suppression by exendin(9-39)amide of glucagon-like peptide-1 insulinotropic action in rats infused with dimethyl ester of succinic acid" Endocrine. 15(3):283-5. Aug. 2001.
Edwards et al. "Glucagon-like peptide 1 has a physiological role in the control of postprandial glucose in humans: studies with the antagonist exendin 9-39"Diabetes. ; 48(1):86-93. Jan. 1999.
Drucker et al. "Biologic actions and therapeutic potential of the proglucagon-derived peptides" Nat Clin Pract Endocrinol Metab. ; 1(1):22-31, Nov. 2005.
Service et al., "Hyperinsulinemic Hypoglycemia with Nesidioblastosis after Gastric-Bypass Surgery" N. Engl. J. Med. (2005) 353:3249.
Patti et al., "Severe hypoglycemia postgastric bypass requiring partial pancreatectomy: evidence for inappropriate insulin secretion and pancreatic islet hyperplasia" Diabetologia (2005) 48:2236.
Meier et al., "Comment to: Patti ME, McMahon G, Mun EC et al. (2005) Severe hypoglycaemia post-gastric bypass requiring partial pancreatectomy: evidence for inappropriate insulin secretion and pancreatic islet hyperplasia. Diabetologia 48:2236-2240" Diabetologia (2006) 49:607.
Scroochi et al., "Glucose intolerance but normal satiety in mice with a null mutation in the glucagon-like peptide 1 receptor gene" Nature Med. (1996) 2:1254.
Toft-Nielsen et al., "Exaggerated secretion of glucagon-like peptide-1 (GLP-1)could cause reactive hypoglycaemia" Diabetologia (1998) 41:2280.
Goldfine et al., "Patients with neuroglycopenia after gastric bypass surgery have exaggerated incretin and insulin secretory responses to a mixed meal", J. Clin. Endocrinol. Metab. (2007) 92:4678.
Palladino et al., "Palladino et al., J. Clin. Endocrinol. Metab. (2009) 94:39", J. Clin. Endocrinol. Metab. (2009) 94:39.
McLaughlin et al., "Reversible hyperinsulinemic hypoglycemia after gastric bypass: a consequence of altered nutrient delivery", J. Clin. Endocrinol. Metab. (2010) 95:1851.
Salehi et al., "Gastric bypass surgery enhances glucagon-like peptide 1-stimulated postprandial insulin secretion in humans", Diabetes (2011) 60:2308.
Calabria et al., "GLP-1 receptor antagonist exendin-(9-39) elevates fasting blood glucose levels in congenital hyperinsulinism owing to inactivating mutations in the ATP-sensitive K+ channel", Diabetes (2012) 61:2585.
Salehi et al., "Blockade of glucagon-like peptide 1 receptor corrects postprandial hypoglycemia after gastric bypass", Gastroenterology (2014) 146: 669.
Calabria et al.,"Postprandial Hypoglycemia in Children after Gastric Surgery: Clinical Characterization and Pathophysiology", *Horm. Res. Paediatr.* (2016) 85:140.
De León et al.. "Exendin-(9-39) corrects fasting hypoglycemia in SUR-1-/—mice by lowering cAMP in pancreatic beta-cells and inhibiting insulin secretion", *J. Biol. Chem.* 283(38): 25786-25793 (2008).
"Amidation", The Free Dictionary, available at https://www.thefreedictionary.com/Amidation, retrieved online on Nov. 21, 2019, 3 pages.
Bantle, J.P., et al., "Hyperinsulinemic Hypoglycemia Developing Late after Gastric Bypass", Obes Surg. vol. 17, https://doi.org/10.1007/s11695-007-9102-6, May 2007, p. 592-595.
Botros, N., et al., "Effect of Carbohydrate Restriction in Patients with Hyperinsulinemic Hypoglycemia after Roux-en-Y Gastric Bypass", Obes Surg. vol. 24, Issue 11, https://doi.org/10.1007/s11695-014-1319-6,Jun. 6, 2014, p. 1850-1855.

(56) References Cited

OTHER PUBLICATIONS

Buchwald, H., et al., "Long term, continuous intravenous heparin administration by an implantable infusion pump in ambulatory patients with recurrent venous thrombosis", Surgery, DOI:https://doi.org/10.5555/uri:pii:0039606080901257, vol. 88, Issue 4, Oct. 1, 1980, p. 507-516.

Calabria, A.C., et al., "Postoperative Surveillance and Detection of Postprandial Hypoglycemia after Fundoplasty in Children", published in final edited form as J Pediatr. vol. 159, No. 4, doi:10/1016/j.jpeds.2011.03.049,597-601. Oct. 2011, 11 pages.

Corywell, W., "Depressive Disorders", Merck Manuals Professional Edition, retrieved on Jun. 11, 2019 from https://www.merckmanuals.com/professional/psychiatric-disorders/mood-disorders/depressive-disorders, p. 1-10.

Cosgrove, K.E., et al., "BPDZ 154 Activates Adenosine 5'-Triphosphate-Sensitive Potassium Channels: *In Vitro* Studies Using Rodent Insulin-Secreting Cells and Islets Isolated from Patients with Hyperinsulinism", The Journal of Clinical Endocrinology and Metabolism, vol. 87, No. 11, DOI:https://doi.org/10.1210/jc.2002-020439, Nov. 1, 2002, 4860-4868.

Craig, C.M., et al. "Critical role for GLP-1 in symptomatic post-bariatric hypoglycaemia", Diabetologia, vol. 60, Issue 3, DOI:https://doi.org/10.1007/s00125-016-4179-x, Published in final edited form on Mar. 2017, p. 531-540.

Craig, C.M., et al., "Efficacy and pharmacokinetics of subcutaneous exendin (9-39) in patients with post-bariatric hypoglycaemia", Diabetes, Obesity and Metabolism, vol. 20, Issue 2, DOI:https://doi.org/10.1111/dom.13078, 2017, p. 1-10.

Davidson, M.B, et al., "Exenatide," Nature Reviews Drug Discovery, vol. 4, DOI:10.1038/nrd1828, Sep. 2005, p. 713-714.

De Leon, D.D., "Effect of Exendin-(9-38) on Glycemic Control in Subjects With Congenital Hyperinsulinism", U.S. National Library of Medicine, ClinicalTrials.gov, retrieved on Nov. 21, 2019 from https://www.clinicaltrials.gov/ct2/show/NCT00571324, 28 pages.

Deary, I.J., et al., "Partitioning the symptoms of hypoglycaemia using multi-sample confirmatory factor analysis", Diabetologia, vol. 35, Issue 8, DOI:https://doi.org/10.1007/BF00401150, 1993, p. 771-777.

Dunne, M.J., et al. "Hyperinsulinism in Infancy: From Basic Science to Clinical Disease", Physiological Reviews, vol. 84, No. 1,DOI:10.1152/physrev.00022.2003, Jan. 2004, p. 239-275.

Eisenberg, D., et al., "ASMBS Position Statement on Postprandial Hyperinsulinemic Hypoglycemia after Bariatric Surgery", Surgery for Obesity and Related Diseases, vol. 13, Issue 3, DOI:https://doi.org/10.1016/j.soard.2016.12.005, 2017, p. 371-378.

Eliasson, L., et al. "SUR1 Regulates PKA-independent cAMP-induced Granule Priming in Mouse Pancreatic B-Cells", J. Gen. Physiol, vol. 121, No. 3, DOI:10.1085/jgp.20028707, Mar. 2003, p. 181-197.

Extended European Search Report dated Nov. 28, 2018 in European Patent Application No. 16800620.3, 5 pages.

Extended European Search Report dated Aug. 30, 2011 in European Application No. 08713063.9, 5 pages.

Extended European Search Report dated Dec. 1, 2014 in European Application No. 14171762.9, 6 pages.

Extended European Search Report dated Jan. 21, 2019 in European Application No. 18201976.0, 6 pages.

Extended European Search Report, dated Mar. 9, 2018, European Patent Application No. 16800621.1, 4 pages.

Final Office action dated Oct. 23, 2019 in U.S. Appl. No. 15/576,647, 12 pages.

Final Office action dated Sep. 25, 2019 in U.S. Appl. No. 15/576,647, 16 pages.

Fournet, J.C., et al., "Unbalanced Expression of 11p15 Imprinted Genes in Focal Forms of Congenital Hyperinsulinism", The Amercian Journal of Pathology, vol. 158, No. 6, Jun. 2001, DOI:https://doi.org/10.1016/S0002-9440(10)64689-5, p. 2177-2184.

Franco, J.V., et al., "A Review of Studies Comparing Three Laparoscopic Procedures in Bariatric Surgery: Sleeve Gastrectomy, Roux-en-Y Gastric Bypass and Adjustable Gastric Banding," OBES SURG, vol. 21, No. 9, DOI:10.1007/s11695-011-0390-5, 2011, p. 1458-1468.

Goodson, J.M., Chapter 6 "Dental Applications" In: Medical Applications of Controlled Release, 1984, vol. 2, p. 116-138.

Gough, S.C.L, "Liraglutide: from clinical trials to clinical practice," Diabetes, Obesity and Metabolism, vol. 14, Issue 2, DOI:https://doi.org/10.1111/j.1463-1326.2012.01576.x, 2012, p. 33-40.

Heber, D., et al., "Endocrine and nutritional management of the post-bariatric surgery patient: an Endocrine Society Clinical Practice Guideline", J Clin Endocrinol Metab. vol. 95, Issue 11, DOI:10.1210/jc.2009-2128, Nov. 2010, p. 4823-4843.

Hepburn,D.A., et al., "Symptoms of acute insulin-induced hypoglycaemia in humans with and without IDDM", Diabetes Care, vol. 14, No. 11, DOI:https://doi.org/10.2337/diacare.14.11.949, Nov. 1991, p. 949-957.

Hofeldt, F.D., "Reactive hypoglycemia", Endocrinology and Metabolism Clinics of North America, vol. 18, No. 1, Mar. 1989, p. 185-201.

Hussain, K., et al., "Medications used in the treatment of hypoglycemia due to congenital hyperinsulinism of infancy (HI)", Pediatric Endocrinology Reviews, vol. 2, Supplement 1, Nov. 2004, p. 163-167.

International Hypoglycaemia Study Group (IHSG), Amiel, S.A., et al., "Glucose concentrations of less than 3.0 mmol/L (54 mg/dL) should be reported in clinical trials: A joint position statement of the American Diabetes Association and the European Association for the Study of Diabetes", Diabetes Care, vol. 40, DOI:10.2337/dc16/2215, Jan. 2017, p. 155-157.

International Preliminary Report on Patentability dated May 21, 2019 in International Patent Application No. PCT/US2017/062838, 5 pages.

International Search Report and Written Opinion dated Aug. 18, 2016 in International Patent Application No. PCT/US2016/033837, 7 pages.

International Search Report and Written Opinion dated Aug. 19, 2016 in International Patent Application No. PCT/US2016/033836, 13 pages.

International Search Report and Written Opinion dated Jan. 23, 2018 in International Patent Application No. PCT/US2017/062838, 8 pages.

International Search Report and Written Opinion dated May 26, 2017 in International Patent Application No. PCT/US2017/020596, 10 pages.

International Search Report and Written Opinion dated Sep. 19, 2008 in International Patent Application No. PCT/US2008/000281, filed Jan. 8, 2008, 8 pages.

Kapoor, R.R., et al., "Advances in the diagnosis and management of hyperinsulinemic hypoglycemia," Nature Clinical Practice Endocrinology & Metabolism, vol. 5, No. 2, DOI:https://doi.org/10.1038/ncpendmet1046, Feb. 2009, p. 101-112.

Kellogg, T.A., et al., "Postgastric bypass hyperinsulinemic hypoglycemia syndrome: characterization and response to a modified diet", Surgery for Obesity and Related Diseases, vol. 4, Issue 4, DOI:10.1016/j.soard.2008.05.005, Jul.-Aug. 2008, p. 492-499.

Kenny, C., "When Hypoclycemia is not obvious: diagnosing and treating under-recognized and undisclosed hypoglycemia", Primary Care Diabetes, vol. 8, Issue 1, DOI:http://dx.doi.org/10.1016/j.pcd.2013.09.002, Apr. 1, 2014, p. 3-11.

Kim, S.H., et al., "Glucose-stimulated insulin secretion in gastric bypass patients with hypoglycemic syndrome: no evidence for inappropriate pancreatic beta-cell function", Obesity Surgery, vol. 20, Issue 8, DOI:https://doi.org/10.1007/s11695-010-0183-2, Aug. 2010, p. 1110-1116.

Laferrere, B., et al., "Effect of weight loss by gastric bypass surgery versus hypocaloric diet on glucose and incretin levels in patients with type 2 diabetes", The Journal of Clinical Endocrinology & Metabolism, vol. 93, Issue 7, DOI:https://doi.org/10.1210/jc.2007-2851, Jul. 2008, p. 2479-2485.

Langa, K.M., et al., "The Diagnosis and Management of Mild Cognitive Impairment: A Clinical Review", JAMA, vol. 312, Issue 23, DOI:https://doi.org/10.1001/jama.2014.13806, Dec. 17, 2014, p. 2551-2561.

(56) References Cited

OTHER PUBLICATIONS

Langer, R., "New Methods of Drug Delivery", Science, vol. 249, Issue 4976, DOI:10.1126/science.2218494, Sep. 28, 1990, p. 1527-1533.

Larraufie, P., et al., "Important Role of the GLP-1 Axis for Glucose Homeostasis after Bariatric Surgery", Cell Reports, DOI:https://doi.org/10.1016/j.celrep.2019.01.047, vol. 26, Issue 6, Feb. 5, 2019, p. 1399-1408.

Lev-Ran, A., et al., "The diagnosis of postprandial hypoglycemia", Diabetes, vol. 30, Issue 12, DOI:10.2337/diab.30.12.996, Dec. 1981, p. 996-999.

Mandal, A., "Defining Hypoglycemia", News Medical: Life Sciences, retrieved on Nov. 20, 2019 from https://www.news-medical.net/health/Defining-Hypoglycemia.aspx, 3 pages.

Manning, S., et al. "GLP-1: A Mediator of the Beneficial Metabolic Effects of Bariatric Surgery?", Physiology, vol. 30, Issue 1, DOI:https://doi.org/10.1152/physiol.00027.2014, Jan. 1, 2015, p. 50-62.

Mechanick, J.I., et al., "Clinical practice guidelines for the perioperative nutritional, metabolic, and nonsurgical support of the bariatric surgery patient-2013 update: cosponsored by American Association of Clinical Endocrinologists", Obesity (Silver Spring), vol. 21, Issue 1, DOI:10.1002/oby.20461, Mar. 2013, 64 pages.

Meijeren, J.V., et al., "Evaluation of carbohydrate restriction as primary treatment for post-gastric bypass hypoglycemia", Surgery for Obesity and Related Diseases, vol. 13, Issue 3, DOI:https://doi.org/10.1016/j.soard.2016.11.004, Mar. 2017, p. 404-410.

Moize, V.L., et al., "Nutritional pyramid for post-gastric bypass patients", Obesity Surgery, vol. 20, Issue 8, DOI:10.1007/s11695-010-0160-9, 2010, p. 1133-1141.

Montrose-Rafizadeh, C. et al. "High Potency Antagonists of the Pancreatic Glucagon-like Peptide-1 Receptor", The Journal of Biological Chemistry, vol. 272, Issue 34, DOI:10.1074/jbc.272.34.21201, Aug. 22, 1997, p. 21201-21206.

Myers, H.R., "Why Does Blood Pressure Drop After a Meal?", Livestrong.com, retrieved on Nov. 21, 2019, from http://www.livestrong.com/article/413792-postprandial-hypoglycemic-diet/, 2 pages.

Nabel, E.G., "Cardiovascular Disease", The New England Journal of Medicine, vol. 349, Issue 1, DOI:10.1056/NEJMra035098, Jul. 3, 2003, p. 60-72.

Ng, D.D., et al. 'Acarbose treatment of postprandial hypoglycemia in children after Nissen fundoplication', The Journal of Pediatrics, vol. 139, Issue 6, DOI:https://doi.org/10.1067/mpd.2001.119169, Dec. 2001, p. 877-879.

Nielsen, P.E., "Peptide nucleic acids as therapeutic agents", Current Opinion in Structural Biology, vol. 9, Issue 3, DOI: https://doi.org/10.1016/S0959-440X(99)80047-5, Jun. 1999, p. 353-357.

Non-Final Office action dated Mar. 21, 2019 in U.S. Appl. No. 15/576,647, 17 pages.

Office Action dated Feb. 22, 2019 in European Patent Application No. 16800621.1, 3 pages.

Palladino, A.A., et al., "Hyperinsulinism in Infancy and Childhood: When an Insulin Level is Not Always Enough", Clinical Chemistry, vol. 54, Issue 2, DOI:10.1373/clinchem.2007.098988, Jan. 2008, p. 256-263.

Palladino, A.A., et al., "Increased Glucagon-Like Peptide-1 secretion and Postprandial Hypoglycemia in Children after Nissen Fundoplication", The Journal of Clinical Endocrinology & Metabolism, vol. 94, Issue 1, DOI:10.1210/jc.2008-1263, Jan. 2009, p. 39-44.

Patti, M., et al., "Hypoglycemia after Gastric Bypass: The Dark Side of GLP-1", Gastroentrology, vol. 146, Issue 3, DOI:10.1053/j.gastro.2014.01.038, Mar. 2014, p. 605-608.

Pramanick, S., et al., "Excipient Selection in Parenteral Formulation Development", Pharma Times, vol. 45, No. 3, Mar. 2013, p. 65-77.

Saudek, C.D., et al., "A Preliminary Trial of the Programmable Implantable Medication System for Insulin Delivery", The New England Journal of Medicine, vol. 321, No. 9, DOI: 10.1056/NEJM198908313210904, Aug. 31, 1989, p. 574-579.

Seaquist, E.R., et al., "Hypoglycemia and Diabetes: A Report of a Workgroup of the American Diabetes Association and The Endocrine Society", Diabetes Care, vol. 36, Issue 5, DOI:https://doi.org/10.2337/dc12-2480 , May 2013, p. 1384-1395.

Seghers, V., et al. "Sur 1 Knockout Mice. A Model for KATP Channel-Independent Regulation of Insulin Secretion", The Journal of Biological Chemistry, vol. 275, No. 13, DOI:10.1074/jbc.275.13.9270, Mar. 31, 2000, p. 9270-9277.

Sefton, M.V., "Implantable Pumps" Critical Reviews in Biomedical Engineering, vol. 14, Issue 3 , p. 201-240.

Service, F.J., et al., "Mean Amplitude of Glycemic Excursions, a Measure of Diabetic Instability", Diabetes, vol. 19, Issue 9, DOI:https://doi.org/10.2337/diab.19.9.644, Sep. 1970, p. 644-655.

Suhl, E., et al., "Medical nutrition therapy for post-bariatric hypoglycemia: practical insights", Surgery for Obesity and Related Diseases, vol. 13, Issue 5, DOI:10.1016/j.soard.2017.01.025, May 2017, p. 888-896.

Tack, J., et al., "Pathophysiology, diagnosis and management of postoperative dumping syndrome", Nature Reviews Gastroenterology & Hepatology, vol. 6, Issue 10, DOI:https://doi.org/10.1038/nrgastro.2009.148, Sep. 1, 2009, p. 583-590.

Tan, M.J., et al., "Repeat subcutaneous dosing of exendin 9-39 reduces hyperinsulinemic hypoglycemia and neuroglycopenic symptoms in patients with post-bariatric hypoglycemia", Poster presentation at the American Diabetes Association's 77th Scientific Sessions, San Diego, CA, Jun. 9-13, 2017, 1 page.

Thanthan, S., et al., "Glucagon-like peptide-1 inhibits insulinotropic effects of oxyntomodulin and glucagon in cattle", Domestic Animal Endocrinology, vol. 42, Issue 3, DOI:https://doi.org/10.1016/j.domaniend.2011.11.004, Apr. 2012, p. 155-164.

Traina, A.N., et al., "Primer on Pramlintide, an Amylin Analog", The Diabetes Educator, vol. 37, Issue 3, DOI:10.1177/0145721711403011, May/Jun. 2011, p. 426-431.

Webb, M., et al., "Growth restriction and exendin 4 promote endocrine expression in cultured islet cells derived from patients with persistent hyperinsulinemic hypoglycemia of infancy (PHHI)", Endocrine Research, vol. 31, Issue 2, DOI:10.1080/07435800500229235, 2005, p. 99-109.

Williard, F.S., et al., "Small Molecule Allosteric Modulation of the Glucagon-Like Peptide-1 Receptor Enhances the Insulinotropic Effect of Oxyntomodulin", Molecular Pharmacology, vol. 82, Issue 6, DOI:https://doi.org/10.1124/mol.112.080432, 2012, p. 1066-1073.

\* cited by examiner

METHODS AND COMPOSITIONS FOR TREATING HYPOGLYCEMIC DISORDERS

CROSS REFERENCE TO RELATED APPLICATIONS

This application is a continuation of U.S. patent application Ser. No. 15/453,823 (now U.S. Pat. No. 10,188,702), filed Mar. 8, 2017, which is a continuation of U.S. patent application Ser. No. 12/081,123 (now U.S. Pat. No. 9,616,108), filed Apr. 10, 2008, which is a continuation-in-part of copending PCT Ser. No. PCT/US08/00281, filed Jan. 8, 2008, which claims priority from U.S. Provisional Application Ser. No. 60/879,033, filed Jan. 8, 2007, each of which is incorporated herein by reference in its entirety.

STATEMENT REGARDING FEDERALLY SPONSORED RESEARCH OR DEVELOPMENT

The invention described herein was supported in whole or in part by grants from The National Institutes of Health (Grant No. 1 K23DK073663-01). The government has certain rights in the invention.

FIELD OF INVENTION

This invention provides methods of treating and ameliorating congenital and neonatal hyperinsulinism and post-prandial hypoglycemia, comprising the step of administering an antagonist of the Glucagon-Like Peptide-1 (GLP-1) receptor, e.g. a GLP-1 fragment or analogue thereof.

BACKGROUND OF THE INVENTION

Congenital hyperinsulinism (HI) is a genetic disorder of pancreatic 3-cell function characterized by failure to suppress insulin secretion in the presence of hypoglycemia, resulting in brain damage or death if inadequately treated. Germline mutations in five genes have been associated with HI: the sulfonylurea receptor (SUR-1, encoded by ABCC8), an inward rectifying potassium channel (Kir6.2, encoded by KCNJII), glucokinase (GCK), glutamate dehydrogenase (GLUD-1), and short-chain L-3-hydroxyacyl-CoA (SCHAD, encoded by HADSC). Loss-of-function mutations in the $K_{ATP}$ channel (composed by two subunits: Kir6.2 and SUR-1) are responsible for the most common and severe form of HI ($K_{ATP}$ HI), with many patients requiring near total pancreatectomy to control hypoglycemia, leading to long hospital stays and life threatening complications.

Post-prandial hypoglycemia is a frequent complication of Nissen fundoplication (e.g. in children), a procedure commonly performed to treat severe gastroesophageal reflux. Up to 30% of patients undergoing this procedure develop dumping syndrome. Dumping syndrome is characterized by early symptoms or "early dumping" due to the fluid shifts provoked by the osmotic load in the small bowel and "late dumping" or post-prandial hypoglycemia. Post-prandial hypoglycemia can also be caused by gastric bypass surgery for obesity.

Effective treatments for congenital HI and post-prandial hypoglycemia are urgently needed.

SUMMARY OF THE INVENTION

This invention provides methods of treating and ameliorating congenital and neonatal hyperinsulinism and post-prandial hypoglycemia, comprising the step of administering an antagonist of the Glucagon-Like Peptide-1 (GLP-1) receptor, e.g. a GLP-1 fragment or analogue thereof.

In one embodiment, the present invention provides a method of treating a subject with congenital hyperinsulinism, comprising the step of administering to the subject an antagonist of the GLP-1 receptor, thereby treating a subject with a congenital hyperinsulinism.

In another embodiment, the present invention provides a method of reducing an incidence of hypoglycemia in a subject with congenital hyperinsulinism, comprising the step of administering to the subject an antagonist of the GLP-1 receptor, thereby reducing an incidence of hypoglycemia in a subject with congenital hyperinsulinism.

In another embodiment, the present invention provides a method of ameliorating a congenital hyperinsulinism in a subject, comprising the step of administering to the subject an antagonist of the GLP-1 receptor, thereby ameliorating a congenital hyperinsulinism in a subject.

In another embodiment, the present invention provides a method of inhibiting a development of a post-prandial hypoglycemia in a subject, comprising the step of administering to the subject an antagonist of the GLP-1 receptor, thereby inhibiting the development of post-prandial hypoglycemia in a subject.

In another embodiment, the present invention provides a method of treating a subject with post-prandial hypoglycemia, comprising the step of administering to the subject an antagonist of the GLP-1 receptor, thereby treating a subject with a post-prandial hypoglycemia.

In another embodiment, the present invention provides a method of reducing an incidence of a post-prandial hypoglycemia in a subject, comprising the step of administering to the subject an antagonist of the GLP-1 receptor, thereby reducing an incidence of a post-prandial hypoglycemia in a subject.

In another embodiment, the present invention provides a method of ameliorating a post-prandial hypoglycemia in a subject, comprising the step of administering to the subject an antagonist of the GLP-1 receptor, thereby ameliorating a post-prandial hypoglycemia in a subject.

In another embodiment, the present invention provides a method of inhibiting a development of a post-prandial hypoglycemia in a subject, comprising the step of administering to the subject an antagonist of the GLP-1 receptor, thereby inhibiting a development of a post-prandial hypoglycemia in a subject.

In another embodiment, the present invention provides a method of treating a subject with a neonatal HI, comprising the step of administering to the subject an antagonist of the GLP-1 receptor, thereby treating a subject with a neonatal HI.

In another embodiment, the present invention provides a method of reducing an incidence of hypoglycemia in a neonate with neonatal HI, comprising the step of administering to the subject an antagonist of the GLP-1 receptor, thereby reducing an incidence of hypoglycemia in a neonate with neonatal HI.

BRIEF DESCRIPTION OF THE FIGURES

The invention will be better understood from a reading of the following detailed description taken in conjunction with the drawings in which like reference designators are used to designate like elements, and in which:

FIG. 1A Fasting blood glucose levels (in mg/dL) in SUR-1$^{-/-}$ mice (n=27) and wild-type littermate controls (n=30), p=0.00000003. FIG. 1B Body weight (in g) in SUR-1$^{-/-}$ mice (n=27) and wild-type littermate controls (n=30). FIG. 1C Oral glucose tolerance (2 g/kg) in SUR-1$^{-/-}$ mice (n=23) (solid line and circles) and wild-type littermate controls (n=25) (dashed line and open squares), p<0.0001, repeated measures ANOVA. FIG. 1D Insulin secretion in response to an oral glucose load (2 g/kg) in SUR-1$^{-/-}$ mice (n=8) (solid line and circles) compared to wild-type littermate controls (n=9) (dashed line and open squares), p=0.02, repeated measures ANOVA;

FIG. 3A Fasting glucagon and insulin levels in vehicle-treated wild-type (n=15) (white bar), exendin-(9-39)-treated wild type (n=14) (hatched bar), vehicle-treated SUR-1$^{-/-}$ (n=13) (black bar), and exendin-(9-39)-treated SUR-1$^{-/-}$ (n=14) (gray bar). FIG. 3B Insulin to glucose ratio in vehicle treated wild-type (n=9) (white bar), exendin-(9-39)-treated wild-type (n=10) (hatched bar), vehicle treated SUR-1$^{-/-}$ (n=9) (black bar), and exendin-(9-39)-treated SUR-1$^{-/-}$ (n=10) (gray bar);

FIG. 4A Oral glucose tolerance in vehicle-treated wild-type littermates (n=10) (dashed line/open squares), exendin-(9-39)-treated wild-type (n=8) (solid line/solid squares), vehicle-treated SUR-1$^{-/-}$ mice (n=9) (dashed line/open circles), and exendin-(9-39)-treated SUR-1$^{-/-}$ (n=9) (solid line/solid circles). Vehicle-treated wild-type vs. vehicle-treated SUR-1$^{-/-}$, p=0.001, repeated measures ANOVA; vehicle-treated SUR-1$^{-/-}$ vs. exendin-(9-39)-treated SUR-1$^{-/-}$ ', p=0.02 at time 120 min. FIG. 4B Insulin sensitivity in vehicle-treated wild-type mice (n=15) (dashed line/open squares), exendin-(9-39)-treated wild-type mice (n=14) (solid line/solid squares), vehicle-treated SUR-1$^{-/-}$ mice (n=13) (dashed line/open circles), and exendin-(9-39)-treated SUR-1$^{-/-}$ mice (n=14) (solid line/solid circles);

DETAILED DESCRIPTION OF THE INVENTION

Figure 1A:
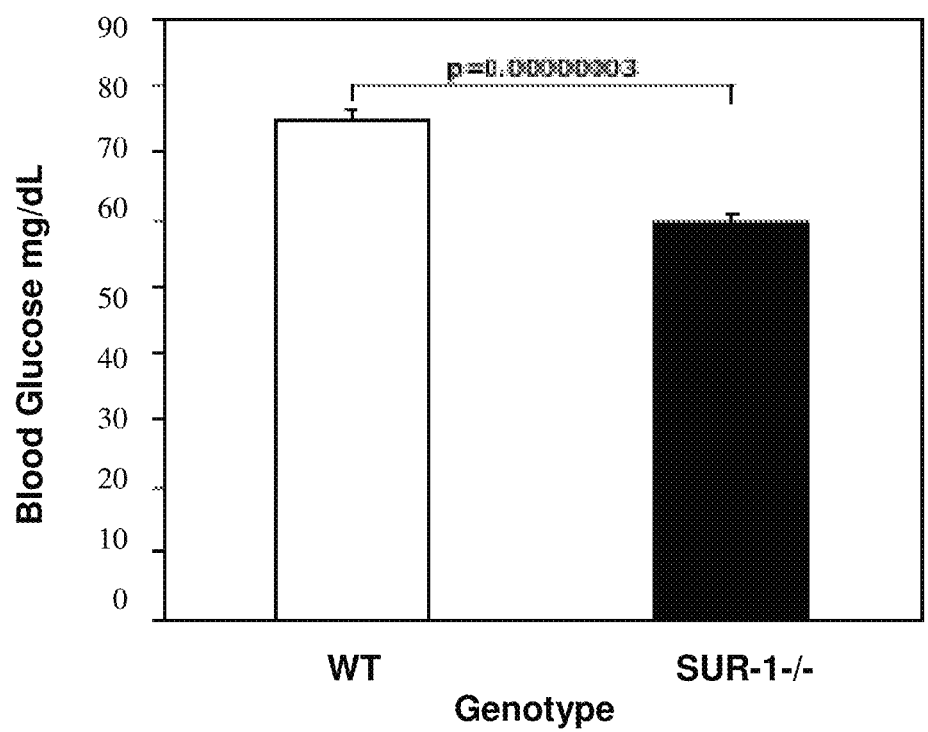
FIGS. 1A-1D show fasting hypoglycemia and impaired glucose tolerance in SUR-1$^{-/-}$ mice.

This invention provides methods of treating and ameliorating congenital and neonatal hyperinsulinism and post-prandial hypoglycemia, comprising the step of administering an antagonist of the Glucagon-Like Peptide-1 (GLP-1) receptor, e.g. a GLP-1 fragment or analogue thereof.

In one embodiment, the present invention provides a method of treating a subject with a congenital hyperinsulinism, comprising the step of administering to the subject an antagonist of the GLP-1 receptor, thereby treating a subject with a congenital hyperinsulinism.

In another embodiment, the present invention provides a method of reducing an incidence of hypoglycemia in a subject with congenital hyperinsulinism, comprising the step of administering to the subject an antagonist of the GLP-1 receptor (GLP-1R), thereby reducing an incidence of hypoglycemia in a subject with congenital hyperinsulinism.

In another embodiment, the present invention provides a method of ameliorating a congenital hyperinsulinism in a subject, comprising the step of administering to the subject an antagonist of GLP-1R, thereby ameliorating a congenital hyperinsulinism in a subject.

In another embodiment, the present invention provides a method of inhibiting a development of hypoglycemia in a subject with congenital hyperinsulinism, comprising the step of administering to the subject an antagonist of GLP-1R, thereby inhibiting a development of hypoglycemia in a subject with congenital hyperinsulinism.

In another embodiment, the present invention provides a method of increasing fasting blood glucose levels and improving fasting tolerance in a subject with congenital hyperinsulinism, comprising the step of administering to the subject an antagonist of GLP-1R, increasing fasting blood glucose levels in a subject with congenital hyperinsulinism.

In one embodiment a continuous infusion of exendin-(9-39) elevated fasting blood glucose levels in normal mice, an effect that has been observed in baboons and healthy human subjects. When administered as a continuous infusion, in another embodiment, exendin-(9-39) significantly raises fasting blood glucose levels in mice harboring a null mutation in SUR-1, without significantly impacting weight gain, glucose tolerance or insulin sensitivity. In another embodiment, elevated insulin/glucose ratio is decreased by exendin-(9-39), indicating that in one embodiment, the effect of exendin-(9-39) is mediated by the islet GLP-1 receptor with no significant impact on other peripheral or central GLP-1 receptor-mediated actions.

In another embodiment, the present invention provides a method of decreasing the glucose requirement to maintain normoglycemia of a subject with congenital hyperinsulinism, comprising the step of administering to the subject an antagonist of GLP-1R, thereby decreasing the glucose requirement to maintain euglycemia of a subject with congenital hyperinsulinism.

In one embodiment, exendin-(9-39) or its analogues and fragments described herein, suppresses amino acid-stimulated insulin secretion. In another embodiment exendin-(9-39) or its analogues and fragments described herein, blocks the abnormal nutrient stimulation of insulin secretion in the absence of functional K$^+$ATP channels. In one embodiment, exendin-(9-39) or its analogues and fragments described herein, decreases basal and amino-acid stimulated insulin secretion and intracellular cAMP accumulation. Accordingly and in one embodiment, exendin-(9-39) corrects the abnormal pattern of insulin secretion responsible for hypoglycemia: basal elevated insulin secretion in the absence of glucose and the amino acid-stimulated insulin secretion.

In another embodiment, the GLP-1R antagonist suppresses insulin secretion by the subject.

As provided herein, patients with $K_{ATP}$ HI hyperinsulinism exhibit hypoglycemia in response to oral protein. Further, exendin-(9-39) increases fasting blood glucose levels in SUR1−/− mice. Thus, the present invention shows that exendin-(9-39) and other GLP-1R antagonists are efficacious in treating congenital hyperinsulinism.

In another embodiment, the GLP-1R antagonist is administered after diagnosis of congenital hyperinsulinism. In another embodiment, the GLP-1R antagonist is administered after identification of a genetic abnormality that predisposes to congenital hyperinsulinism. In another embodiment, the GLP-1R antagonist is administered to a subject with a family history of congenital hyperinsulinism. Each possibility represents a separate embodiment of the present invention.

In one embodiment, cyclic AMP stimulates exocytosis by PKA-dependent pathways, through phosphorylation of downstream targets including the KATP channel, and by PKA-independent mechanisms, through the activation of guanine nucleotide exchange factors (GEFs) such as cAMP-GEFII (also known as Epac). The PKA-independent pathway is critical in another embodiment in the potentiation of insulin secretion by the incretin hormones GLP-1 and GIP and in one embodiment, exerts its effect on insulin containing secretory granules located in the readily releasable pool. In pancreatic islets, the effect of cAMPGEFII on insulin secretion depends in one embodiment on cytosolic calcium as well as cAMP, and cAMP sensitizes in another embodiment the exocytotic machinery to calcium. In one embodiment, the inhibition of insulin secretion in SUR-1$^{-/-}$ islets by exendin-(9-39) or its analogues and fragments described herein, is mediated by the effect of cAMP on a late calcium-dependent step in the exocytotic pathway involving the readily releasable pool of insulin granules (FIG. 7).

Figure 7:
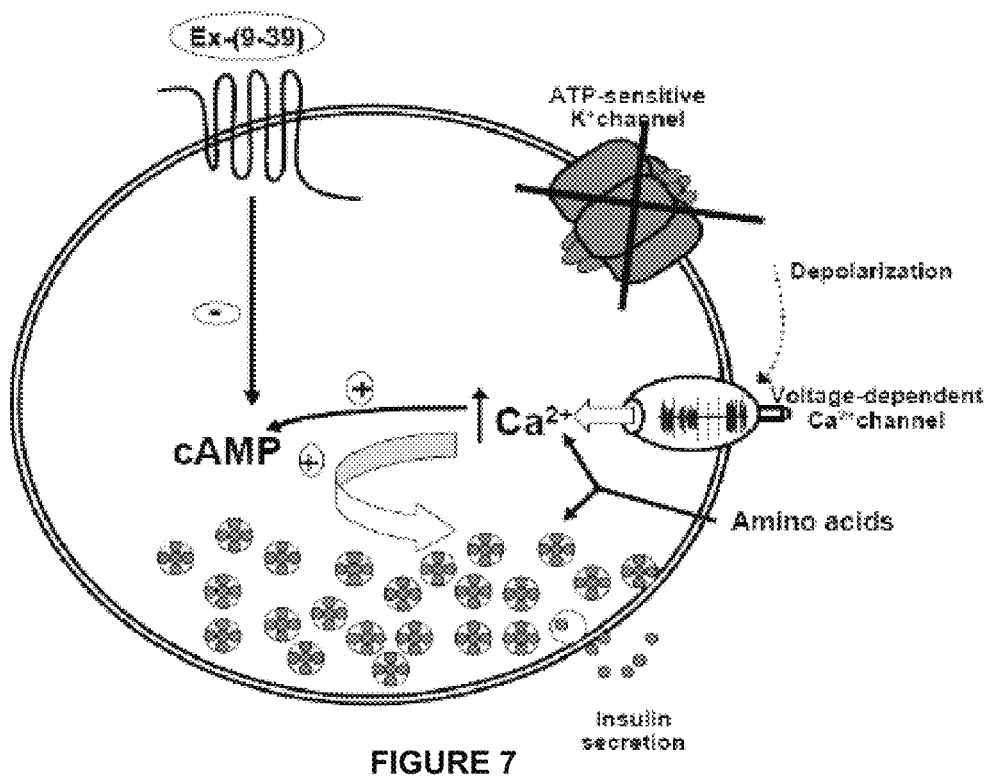
FIG. 7 shows a schematic describing the proposed mechanism of action of exendin-(9-39) in SUR-1$^{-/-}$ islets. In SUR-1$^{-/-}$ mouse islets, plasma membrane depolarization results in elevated cytosolic $Ca^{2+}$ and dysregulated insulin secretion. Exendin-(9-39) binds to the GLP-1 receptor and lowers baseline cAMP levels, resulting in decreased insulin secretion despite the elevated calcium levels. Similarly, by decreasing amino acid-stimulated cAMP accumulation, exendin-(9-39) inhibits amino acid-stimulated insulin secretion.

FIG. 7 shows a schematic describing the proposed mechanism of action of exendin-(9-39) in SUR-1$^{-/-}$ islets. In SUR-1$^{-/-}$ mouse islets, plasma membrane depolarization results in elevated cytosolic Ca$^{2+}$ and dysregulated insulin secretion. Exendin-(9-39) binds to the GLP-1 receptor and lowers baseline cAMP levels, resulting in decreased insulin secretion despite the elevated calcium levels. Similarly, by decreasing amino acid-stimulated cAMP accumulation, exendin-(9-39) inhibits amino acid-stimulated insulin secretion.

The congenital hyperinsulinism treated or ameliorated by methods of the present invention, is, in another embodiment, associated with increases insulin secretion by the subject. In another embodiment, the congenital hyperinsulinism is associated with a genetic abnormality. In another embodiment, the congenital hyperinsulinism is associated with a genetic mutation. In another embodiment, the congenital hyperinsulinism is a result of a genetic abnormality. In another embodiment, the congenital hyperinsulinism is a result of a genetic mutation. Each possibility represents another embodiment of the present invention.

In another embodiment, the congenital hyperinsulinism is associated with a KATP channel dysfunction. In another embodiment, the congenital hyperinsulinism is a $K_{ATP}$ hyperinsulinism.

In another embodiment, the congenital hyperinsulinism is associated with a mutation in a gene encoding a sulfonylurea receptor (ABCC8). In another embodiment, the congenital hyperinsulinism is associated with a mutation in a gene encoding an inward rectifying potassium channel, Kir6.2 protein (KCNJII). In another embodiment, the congenital hyperinsulinism is associated with a mutation in a gene encoding a glucokinase (GCK). In another embodiment, the congenital hyperinsulinism is associated with a mutation in a gene encoding a glutamate dehydrogenase (GLUD-1). In another embodiment, the congenital hyperinsulinism is associated with a mutation in a gene encoding a mitochondrial enzyme short-chain 3-hydroxyacyl-CoA dehydrogenase (HADHSC). In another embodiment, the congenital hyperinsulinism is associated with any other mutation known in the art to be associated with a congenital hyperinsulinism. Each possibility represents another embodiment of the present invention.

In another embodiment, the present invention provides a method of treating a subject with a post-prandial hypoglycemia, comprising the step of administering to the subject an antagonist of the GLP-1 receptor, thereby treating a subject with a post-prandial hypoglycemia.

In another embodiment, the present invention provides a method of reducing an incidence of a post-prandial hypoglycemia in a subject, comprising the step of administering to the subject an antagonist of GLP-1R, thereby reducing an incidence of a post-prandial hypoglycemia in a subject.

In another embodiment, the present invention provides a method of ameliorating a post-prandial hypoglycemia in a subject, comprising the step of administering to the subject an antagonist of GLP-1R, thereby ameliorating a post-prandial hypoglycemia in a subject.

In another embodiment, the present invention provides a method of inhibiting a development of a post-prandial hypoglycemia in a subject, comprising the step of administering to the subject an antagonist of GLP-1R, thereby inhibiting a development of a post-prandial hypoglycemia in a subject.

In another embodiment, the present invention provides a method of decreasing the glucose requirement to maintain euglycemia of a subject with post-prandial hypoglycemia, comprising the step of administering to the subject an antagonist of GLP-1R, thereby decreasing the glucose requirement to maintain euglycemia of a subject with post-prandial hypoglycemia.

In another embodiment, the GLP-1R antagonist suppresses insulin secretion by the subject.

As provided herein, post-prandial hypoglycemia after Nissen fundoplication are characterized by high insulin and GLP-1 levels following oral glucose load. Further, exendin-(9-39) antagonizes GLP-1 signaling. Thus, the present invention shows that exendin-(9-39) and other GLP-1R antagonists are efficacious in treating post-prandial hypoglycemia (e.g. in response to Nissen fundoplication or gastric-bypass surgery).

The post-prandial hypoglycemia treated or inhibited by methods and compositions of the present invention is, in another embodiment, associated with a Nissen fundoplication. In another embodiment, the post-prandial hypoglycemia occurs following a Nissen fundoplication. Each possibility represents a separate embodiment of the present invention.

In another embodiment, the post-prandial hypoglycemia is associated with a gastric-bypass surgery. In another embodiment, the post-prandial hypoglycemia occurs following a gastric-bypass surgery. Each possibility represents a separate embodiment of the present invention.

In another embodiment, the GLP-1R antagonist is administered after diagnosis of post-prandial hypoglycemia.

In another embodiment, the GLP-1R antagonist is administered after a gastric-bypass surgery. In another embodiment, the GLP-1R antagonist is administered during a gastric-bypass surgery. In another embodiment, the GLP-1R antagonist is administered prior to a gastric-bypass surgery.

In another embodiment, the GLP-1R antagonist is administered after a Nissen fundoplication. In another embodiment, the GLP-1R antagonist is administered during a Nissen fundoplication. In another embodiment, the GLP-1R antagonist is administered prior to a Nissen fundoplication.

In another embodiment, the present invention provides a method of treating a subject with a neonatal HI, comprising the step of administering to the subject an antagonist of the GLP-1 receptor, thereby treating a subject with a neonatal HI.

In another embodiment, the present invention provides a method of reducing an incidence of hypoglycemia in a subject with neonatal HI, comprising the step of administering to the subject an antagonist of the GLP-1 receptor, thereby reducing an incidence of hypoglycemia in a subject with neonatal HI.

The neonatal hyperinsulinism (HI) treated or ameliorated by methods of the present invention, is, in another embodiment, non-genetic HI. In another embodiment, the neonatal HI is prolonged neonatal HI. In another embodiment, the neonatal HI is non-genetic, prolonged neonatal HI. In another embodiment, the neonatal HI lasts for several months after birth. In another embodiment, the neonatal HI is the result of peri-natal stress. In another embodiment, the peri-natal stress is the result of small-for-gestational-age birth weight. In another embodiment, the peri-natal stress is the result of birth asphyxia. In another embodiment, the peri-natal stress is the result of any other peri-natal stress known in the art. Each possibility represents a separate embodiment of the present invention.

The GLP-1R antagonist utilized in methods and compositions of the present invention is, in another embodiment, a GLP-1 analogue. In another embodiment, the analogue is an antagonist of a GLP-1R. Each possibility represents a separate embodiment of the present invention.

In another embodiment, the analogue is resistant to cleavage by dipeptidyl peptidase-IV (DPPIV). In another embodiment, the analogue exhibits an extended biological half-life relative to GLP-1. In another embodiment, the analogue is resistant to degradation by DPPIV. Each possibility represents another embodiment of the present invention.

"Resistant to cleavage" refers, in another embodiment, to resistance to proteolysis by DPPIV relative to GLP-1. In another embodiment, the term refers to resistance relative to a GLP-1 fragment. In another embodiment, the term refers to resistance to proteolysis by another dipeptidyl peptidase. In another embodiment, the dipeptidyl peptidase is DPP10 (dipeptidyl peptidase IV-related protein 3). In another embodiment, the dipeptidyl peptidase is DPP7. In another embodiment, the dipeptidyl peptidase is DPP6. In another embodiment, the dipeptidyl peptidase is DPP3. In another embodiment, the dipeptidyl peptidase is DPP9. In another embodiment, the dipeptidyl peptidase is any other dipeptidyl peptidase known in the art. In another embodiment, the term refers to resistance to proteolysis by any other protease known in the art. In another embodiment, the term refers to any other definition of "protease resistant" known in the art. Each possibility represents a separate embodiment of the present invention.

In another embodiment, the GLP-1R antagonist utilized in methods and compositions of the present invention exhibits an improvement in a desirable biological property relative to GLP-1. In another embodiment, the biological property is improved biological half-life. In another embodiment, the biological property is improved affinity for GLP-1R. In another embodiment, the biological property is improved potency for antagonism of GLP-1R. In another embodiment, the biological property is any other desirable biological property known in the art. Each possibility represents a separate embodiment of the present invention.

In another embodiment, the GLP-1R antagonist comprises an amide group on its C-terminus (e.g. the end of a peptide that usually contains a carboxy group). In another embodiment, the amide group confers an improvement in a desirable biological property upon the antagonist. In another embodiment, the property is resistance to proteolysis. In another embodiment, the biological property is improved biological half-life. In another embodiment, the biological property is improved affinity for GLP-1R. In another embodiment, the biological property is improved potency for antagonism of GLP-1R. In another embodiment, the biological property is any other desirable biological property known in the art. Each possibility represents a separate embodiment of the present invention.

In another embodiment, the antagonist is an exendin (9-39) (Ex9-39) peptide. In another embodiment, the peptide is also known as "exendin-3." In another embodiment, the peptide has a sequence set forth in SEQ ID No: 1. In another embodiment, the antagonist is a fragment of the peptide set forth in SEQ ID No. 1. In another embodiment, the fragment is an antagonist of a GLP-1R. In another embodiment, the fragment exhibits an extended biological half-life relative to GLP-1. In another embodiment, the fragment is resistant to cleavage by DPPIV. In another embodiment, the fragment is resistant to degradation by DPPIV. Each possibility represents another embodiment of the present invention.

In another embodiment, the antagonist is Exendin (9-39). In another embodiment, the exendin9-39 peptide has the sequence: DLSKQMEEEAVRLFIEWLKNGGPSSGAP-PPS-amide (SEQ ID No: 1). In another embodiment, the exendin 9-39 peptide is a homologue of SEQ ID No: 1. In another embodiment, the exendin9-39 peptide is an analogue of SEQ ID No: 1. In another embodiment, the exendin9-39 peptide is a variant of SEQ ID No: 1. In another embodiment, the exendin9-39 peptide is any other exendin9-39 peptide known in the art. Each possibility represents a separate embodiment of the present invention.

In another embodiment, the antagonist is a fragment of an exendin protein. In another embodiment, the exendin protein has the sequence: MKIILWLCVFGLFLATLF-PVSWQMPVE SGLSSEDSASSESFASKIKRHSDGTFTS-DLSKQMEEEAVRLFIEWLKNGGPSSGAPPPSG (SEQ ID No: 2).

In another embodiment, the exendin protein is a homologue of SEQ ID No: 2. In another embodiment, the exendin protein is an analogue of SEQ ID No: 2. In another embodiment, the exendin protein is a variant of SEQ ID No: 2. In another embodiment, the exendin protein is any other exendin protein known in the art. Each possibility represents a separate embodiment of the present invention.

In another embodiment, the GLP-1R antagonist is a GLP-1 (9-36) amide. In another embodiment, the sequence of the GLP-1R antagonist is:

HAEGTFTSDVSSYLEGQAAKEFIAWLVKGR (SEQ ID No: 9). In another embodiment, the GLP-1R antagonist is a homologue of SEQ ID No: 9. In another embodiment, the GLP-1R antagonist is an analogue of SEQ ID No: 9. In another embodiment, the GLP-1R antagonist is a variant of SEQ ID No: 9. In another embodiment, the GLP-1R antagonist is any other GLP-1 (9-36) amide known in the art. Each possibility represents a separate embodiment of the present invention.

In another embodiment, the GLP-1R antagonist is a GLP-1 (7-36) amide containing a mutation. In another embodiment, the mutation confers GLP-1R antagonistic activity. In another embodiment, the mutation reduces or eliminates GLP-1R agonistic activity. In another embodiment, the mutation does not reduce binding to GLP-1R. In another embodiment, the mutation is a substitution. In another embodiment, the mutation is an insertion. In another embodiment, the mutation is a deletion. In another embodiment, the mutation is a Glu9Lys mutation. In another embodiment, the mutation is any other type of mutation known in the art. Each possibility represents a separate embodiment of the present invention.

In another embodiment, the GLP-1 (7-36) that is modified has the sequence HAEGTFTSDVSSYLEGQAAKEFI-AWLVKGR (SEQ ID No: 5). In another embodiment, the GLP-1 (7-36) is a homologue of SEQ ID No: 5. In another embodiment, the GLP-1 (7-36) is an analogue of SEQ ID No: 5. In another embodiment, the GLP-1 (7-36) is a variant of SEQ ID No: 5. In another embodiment, the GLP-1 (7-36) is any other GLP-1 (7-36) amide known in the art. Each possibility represents a separate embodiment of the present invention.

In another embodiment, the sequence of the GLP-1R antagonist is:

HAEGTFTSKVSSYLEGQAAKEFIAWLVKGR (SEQ ID No: 6). In another embodiment, the GLP-1R antagonist is a homologue of SEQ ID No: 6. In another embodiment, the GLP-1R antagonist is an analogue of SEQ ID No: 6. In another embodiment, the GLP-1R antagonist is a variant of SEQ ID No: 6. In another embodiment, the GLP-1R antagonist is any other mutated GLP-1 (7-36) amide known in the art. Each possibility represents a separate embodiment of the present invention.

In another embodiment, the GLP-1R antagonist is an Exendin-4 containing a mutation. In another embodiment, the mutation confers GLP-1R antagonistic activity. In another embodiment, the mutation reduces or eliminates GLP-1R agonistic activity. In another embodiment, the mutation does not reduce binding to GLP-1R. In another embodiment, the mutation is a substitution. In another embodiment, the mutation is an insertion. In another embodiment, the mutation is a deletion. In another embodiment, the mutation is a des-His1 mutation. In another embodiment, the mutation is a Glu9 substitution. In another embodiment, the mutation is a des-His1-Glu9 mutation. In another embodiment, the mutation is any other type of mutation known in the art. Each possibility represents a separate embodiment of the present invention.

In another embodiment, the Exendin-4 that is modified has the sequence:

HGEGTFTSDLSKQMEEEAVRLFIEWLKNGGPSS-GAPPPS-NH2 (SEQ ID No: 7). In another embodiment, the Exendin-4 is a homologue of SEQ ID No: 7. In another embodiment, the Exendin-4 is an analogue of SEQ ID No: 7. In another embodiment, the Exendin-4 is a variant of SEQ ID No: 7. In another embodiment, the Exendin-4 is any other Exendin-4 known in the art. Each possibility represents a separate embodiment of the present invention.

In another embodiment, the sequence of the GLP-1R antagonist is:

GEGTFTSELSKQMEEEAVRLFIEWLKNGGPSSGAP-PPS-NH2 (SEQ ID No: 8). In another embodiment, the GLP-1R antagonist is a homologue of SEQ ID No: 8. In another embodiment, the GLP-1R antagonist is an analogue of SEQ ID No: 8. In another embodiment, the GLP-1R antagonist is a variant of SEQ ID No: 8. In another embodiment, the GLP-1R antagonist is any other mutated Exendin-4 known in the art. Each possibility represents a separate embodiment of the present invention.

In another embodiment, the sequence of the GLP-1R antagonist is:

GEGTFTSQLSKQMEEEAVRLFIEWLKNGGPSSGAP-PPS-NH2 (SEQ ID No: 3). In another embodiment, the GLP-1R antagonist is a homologue of SEQ ID No: 3. In another embodiment, the GLP-1R antagonist is an analogue of SEQ ID No: 3. In another embodiment, the GLP-1R antagonist is a variant of SEQ ID No: 3. Each possibility represents a separate embodiment of the present invention.

In another embodiment, the sequence of the GLP-1R antagonist is:

KRHSDGTFTSDLSKQMEEEAVRLFIEWLKNG-GPSSGAPPPS (SEQ ID No: 4). In another embodiment, the GLP-1R antagonist is a homologue of SEQ ID No: 4. In another embodiment, the GLP-1R antagonist is an analogue of SEQ ID No: 4. In another embodiment, the GLP-1R antagonist is a variant of SEQ ID No: 4. Each possibility represents a separate embodiment of the present invention.

In another embodiment, the sequence of the antagonist is:

HSDGTFTSDLSKGMEEEAVRLFIEWLKNGGPSS-GAPPPS-amide (SEQ ID No: 10). In another embodiment, the GLP-1R antagonist is a homologue of SEQ ID No: 10. In another embodiment, the GLP-1R antagonist is an analogue of SEQ ID No: 10. In another embodiment, the GLP-1R antagonist is a variant of SEQ ID No: 10. Each possibility represents a separate embodiment of the present invention.

In another embodiment, the GLP-1R antagonist is precursor of 1 of the above GLP-1R antagonists. In another embodiment, the precursor is metabolized in the subject's body to generate the active compound. In another embodiment, the active compound is generated via any other process known in the art. Each possibility represents a separate embodiment of the present invention.

In another embodiment, a GLP-1R antagonist of methods and compositions of the present invention is a mimetic of GLP-1. In another embodiment, the antagonist is a mimetic of Ex9-39. In another embodiment, the mimetic is an antagonist of a GLP-1R. In another embodiment, the mimetic exhibits protease resistance relative to GLP-1. In another embodiment, the mimetic exhibits protease resistance relative to a GLP-1 fragment (e.g. the GLP-1 fragment upon which the mimetic was modeled). In another embodiment, the mimetic is resistant to degradation by DPPIV. Each possibility represents another embodiment of the present invention.

In another embodiment, a mimetic compound of the present invention is derived from an exendin peptide or GLP-1 peptide by incorporating 1 or more modified AA residues. In another embodiment, one or more of the termini is derivatized to include a blocking group, i.e. a chemical substituent suitable to protect and/or stabilize the N- and C-termini from undesirable degradation. In another embodiment, "undesirable degradation" refers to any type of enzymatic, chemical or biochemical breakdown of the compound at its termini which is likely to affect the function of the compound, i.e. sequential degradation of the compound at a terminal end thereof.

In another embodiment, blocking groups include protecting groups conventionally used in the art of peptide chemistry which will not adversely affect the in vivo activities of the peptide. For example, suitable N-terminal blocking groups can be introduced by alkylation or acylation of the N-terminus. Examples of suitable N-terminal blocking groups include $C_1$-$C_5$ branched or unbranched alkyl groups, acyl groups such as formyl and acetyl groups, as well as substituted forms thereof, such as the acetamidomethyl (Acm) group. Desamino AA analogs are also useful N-terminal blocking groups, and can either be coupled to the N-terminus of the peptide or used in place of the N-terminal reside. Suitable C-terminal blocking groups, in which the carboxyl group of the C-terminus is either incorporated or not, include esters, ketones or amides. Ester or ketone-forming alkyl groups, particularly lower alkyl groups such as methyl, ethyl and propyl, and amide-forming amino groups such as primary amines (—$NH_2$), and mono- and di-alkyl amino groups such as methyl amino, ethylamino, dimethylamino, diethylamino, methylethylamino and the like are examples of C-terminal blocking groups. Descarboxylated AA analogues such as agmatine are also useful C-terminal blocking groups and can be either coupled to the peptide's C-terminal residue or used in place of it. In another embodiment, the free amino and carboxyl groups at the termini are removed altogether from the peptide to yield desamino and descarboxylated forms thereof without affect on peptide activity.

In another embodiment, a mimetic compound of the present invention is derived from an exendin peptide or GLP-1 peptide by another modification. In another embodiment, such modifications include, but are not limited to, substitution of 1 or more of the AA in the natural L-isomeric form with D-isomeric AA. In another embodiment, the peptide includes one or more D-amino acid resides, or comprises AA that are all in the D-form. Retro-inverso forms of peptides in accordance with the present invention are also contemplated, for example, inverted peptides in which all AA are substituted with D-amino acid forms.

In another embodiment, mimetic compounds of the present invention are acid addition salts of an exendin peptide or GLP-1 peptide. In another embodiment, an exendin peptide or GLP-1 peptide is treated with an inorganic acid such as hydrochloric, hydrobromic, sulfuric, nitric, phosphoric, and the like, or an organic acid such as an acetic, propionic, glycolic, pyruvic, oxalic, malic, malonic, succinic, maleic, fumaric, tataric, citric, benzoic, cinnamie, mandelic, methanesulfonic, ethanesulfonic, p-toluenesulfonic, salicyclic and the like, to provide a water soluble salt of the peptide suitable for use in the invention.

In another embodiment, a mimetic compound of the present invention is produced by a process comprising the step of in vivo or in vitro chemical derivatization of an exendin peptide or GLP-1 peptide, e.g., acetylation, or carboxylation. Also included are modifications of glycosylation, e.g., those made by modifying the glycosylation patterns of a polypeptide during its synthesis and processing or in further processing steps; e.g., by exposing the polypeptide to enzymes which affect glycosylation, e.g., mammalian glycosylating or deglycosylating enzymes. In another embodiment, a mimetic compound of the present invention comprises a phosphorylated AA residue, e.g., phosphotyrosine, phosphoserine, or phosphothreonine.

In another embodiment, a mimetic compound of the present invention is produced by modifying an exendin peptide or GLP-1 peptide using ordinary molecular biological techniques so as to improve it resistance to proteolytic degradation or to optimize solubility properties. In another embodiment, an exendin peptide or GLP-1 peptide is modified to render it more suitable as a therapeutic agent. Analogs of such polypeptides include those containing residues other than naturally occurring L-amino acids, e.g., D-amino acids or non-naturally occurring synthetic amino acids. The peptides of the invention are not limited to products of any of the specific exemplary processes listed herein.

Methods of identifying mimetic compounds are well known in the art, and are described, for example, in Song J et al, Biochem Cell Biol 76(2-3): 177-188, 1998; Vogt A et al, J Biol Chem. 270(2): 660-4, 1995; Alexopoulos K et al, J Med Chem 47(13): 3338-52, 2004; Andronati S A et al, Curr Med Chem 11(9): 1183-211, 2004; Breslin M J et al, Bioorg Med Chem Lett 13(10): 1809-12, 2003; and WO 02/081649 ("ErbB interface peptidomimetics and methods of use thereof") in the name of Greene et al. In another embodiment, model building is used to design the mimetic compounds as described in one of the above references. In another embodiment, solubility of the mimetic compounds is optimized as described in one of the above references. Each possibility represents a separate embodiment of the present invention.

In another embodiment, the GLP-1 mimetic utilized in methods and compositions of the present invention exhibits an improvement in a desirable biological property relative to GLP-1. In another embodiment, the mimetic exhibits improvement in a desirable biological property relative to a GLP-1 fragment (e.g. the GLP-1 fragment upon which the mimetic was modeled). In another embodiment, the biological property is improved biological half-life. In another embodiment, the biological property is improved affinity for GLP-1R. In another embodiment, the biological property is improved oral availability. In another embodiment, the biological property is improved selectivity for inhibiting insulin secretion. In another embodiment, the biological property is improved potency for antagonism of GLP-1R. In another embodiment, the biological property is any other desirable biological property known in the art. Each possibility represents a separate embodiment of the present invention.

In another embodiment, the subject of methods and compositions of the present invention is a human subject. In another embodiment, the subject is a pediatric subject. In another embodiment, the subject is a child. In another embodiment, the subject is a juvenile. In another embodiment, the subject is a baby. In another embodiment, the subject is an infant. In another embodiment, the subject is an adolescent. In another embodiment, the subject is an adult. In another embodiment, the subject is any other type of subject known in the art. Each possibility represents a separate embodiment of the present invention.

In another embodiment, the subject is under 10 years of age. In another embodiment, the age is under 9 years. In another embodiment, the age is under 8 years. In another embodiment, the age is under 7 years. In another embodiment, the age is under 6 years. In another embodiment, the age is under 5 years. In another embodiment, the age is under 4 years. In another embodiment, the age is under 3 years. In another embodiment, the age is under 2 years. In another embodiment, the age is under 18 months. In another embodiment, the age is under 1 year. In another embodiment, the age is under 10 months. In another embodiment, the age is under 8 months. In another embodiment, the age is under 6 months. In another embodiment, the age is under 4 months. In another embodiment, the age is under 3 months. In another embodiment, the age is under 2 months. In another embodiment, the age is under 1 month.

In another embodiment, the age is over 6 months. In another embodiment, the age is over 1 year. In another embodiment, the age is over 2 years. In another embodiment, the age is over 3 years. In another embodiment, the age is over 5 years. In another embodiment, the age is over 7 years. In another embodiment, the age is over 10 years. In another embodiment, the age is over 15 years. In another embodiment, the age is over 20 years. In another embodiment, the age is over 30 years. In another embodiment, the age is over 40 years. In another embodiment, the age is over 50 years. In another embodiment, the age is over 60 years. In another embodiment, the age is over 65 years. In another embodiment, the age is over 70 years.

In another embodiment, the age is 1 month-5 years. In another embodiment, the age is 2 months-5 years. In another embodiment, the age is 3 months-5 years. In another embodiment, the age is 4 months-5 years. In another embodiment, the age is 6 months-5 years. In another embodiment, the age is 9 months-5 years. In another embodiment, the age is 1-5 years. In another embodiment, the age is 2-5 years. In another embodiment, the age is 3-5 years. In another embodiment, the age is 1-10 years. In another embodiment, the age is 1-5 years. In another embodiment, the age is 2-10 years. In another embodiment, the age is 3-10 years. In another embodiment, the age is 5-10 years. In another embodiment, the age is 1-6 months. In another embodiment, the age is 2-6 months. In another embodiment, the age is 3-12 months. In another embodiment, the age is 6-12 months.

Each age and age range represents a separate embodiment of the present invention.

In another embodiment, the GLP-1R antagonist of methods and compositions of the present invention is administered by infusion. In another embodiment, the method of administration comprises a pump.

The pharmaceutical compositions containing the GLP-1R antagonist can be, in another embodiment, administered to a subject by any method known to a person skilled in the art, such as parenterally, transmucosally, transdermally, intra-muscularly, intravenously, intra-dermally, subcutaneously, intra-peritonealy, intra-ventricularly, intra-cranially, intra-vaginally or intra-tumorally.

In another embodiment of methods and compositions of the present invention, the pharmaceutical compositions are administered orally, and are thus formulated in a form suitable for oral administration, i.e. as a solid or a liquid preparation. Suitable solid oral formulations include tablets, capsules, pills, granules, pellets and the like. Suitable liquid oral formulations include solutions, suspensions, dispersions, emulsions, oils and the like. In another embodiment of the present invention, the active ingredient is formulated in a capsule. In accordance with this embodiment, the compositions of the present invention comprise, in addition to the active compound and the inert carrier or diluent, a hard gelating capsule.

In another embodiment, the pharmaceutical compositions are administered by intravenous, intra-arterial, or intra-muscular injection of a liquid preparation. Suitable liquid formulations include solutions, suspensions, dispersions, emulsions, oils and the like. In another embodiment, the pharmaceutical compositions are administered intravenously and are thus formulated in a form suitable for intravenous administration. In another embodiment, the pharmaceutical compositions are administered intra-arterially and are thus formulated in a form suitable for intra-arterial administration. In another embodiment, the pharmaceutical compositions are administered intra-muscularly and are thus formulated in a form suitable for intra-muscular administration.

In another embodiment, the pharmaceutical compositions are administered topically to body surfaces and are thus formulated in a form suitable for topical administration. Suitable topical formulations include gels, ointments, creams, lotions, drops and the like. For topical administration, the GLP-1R antagonist or its physiologically tolerated derivatives such as salts, esters, N-oxides, and the like are prepared and applied as solutions, suspensions, or emulsions in a physiologically acceptable diluent with or without a pharmaceutical carrier.

In another embodiment, the pharmaceutical composition is administered as a suppository, for example a rectal suppository or a urethral suppository. In another embodiment, the pharmaceutical composition is administered by subcutaneous implantation of a pellet. In another embodiment, the pellet provides for controlled release of GLP-1R antagonist over a period of time.

In another embodiment, the active compound is delivered in a vesicle, e.g. a liposome.

In other embodiments, carriers or diluents used in methods of the present invention include, but are not limited to, a gum, a starch (e.g. corn starch, pregeletanized starch), a sugar (e.g., lactose, mannitol, sucrose, dextrose), a cellulosic material (e.g. microcrystalline cellulose), an acrylate (e.g. polymethylacrylate), calcium carbonate, magnesium oxide, talc, or mixtures thereof.

In other embodiments, pharmaceutically acceptable carriers for liquid formulations are aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of animal, vegetable, or synthetic origin, for example, peanut oil, soybean oil, olive oil, sunflower oil, fish-liver oil, another marine oil, or a lipid from milk or eggs.

In another embodiment, parenteral vehicles (for subcutaneous, intravenous, intraarterial, or intramuscular injection) include sodium chloride solution, Ringer's dextrose, dextrose and sodium chloride, lactated Ringer's and fixed oils. Intravenous vehicles include fluid and nutrient replenishers, electrolyte replenishers such as those based on Ringer's dextrose, and the like. Examples are sterile liquids such as water and oils, with or without the addition of a surfactant and other pharmaceutically acceptable adjuvants. In general, water, saline, aqueous dextrose and related sugar solutions, and glycols such as propylene glycols or polyethylene glycol are preferred liquid carriers, particularly for injectable solutions. Examples of oils are those of animal, vegetable, or synthetic origin, for example, peanut oil, soybean oil, olive oil, sunflower oil, fish-liver oil, another marine oil, or a lipid from milk or eggs.

In other embodiments, the compositions further comprise binders (e.g. acacia, cornstarch, gelatin, carbomer, ethyl cellulose, guar gum, hydroxypropyl cellulose, hydroxypropyl methyl cellulose, povidone), disintegrating agents (e.g.

cornstarch, potato starch, alginic acid, silicon dioxide, croscarmelose sodium, crospovidone, guar gum, sodium starch glycolate), buffers (e.g., Tris-HCL, acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g. sodium lauryl sulfate), permeation enhancers, solubilizing agents (e.g., glycerol, polyethylene glycerol), anti-oxidants (e.g., ascorbic acid, sodium metabisulfite, butylated hydroxyanisole), stabilizers (e.g. hydroxypropyl cellulose, hyroxypropylmethyl cellulose), viscosity increasing agents (e.g. carbomer, colloidal silicon dioxide, ethyl cellulose, guar gum), sweeteners (e.g. aspartame, citric acid), preservatives (e.g., Thimerosal, benzyl alcohol, parabens), lubricants (e.g. stearic acid, magnesium stearate, polyethylene glycol, sodium lauryl sulfate), flow-aids (e.g. colloidal silicon dioxide), plasticizers (e.g. diethyl phthalate, triethyl citrate), emulsifiers (e.g. carbomer, hydroxypropyl cellulose, sodium lauryl sulfate), polymer coatings (e.g., poloxamers or poloxamines), coating and film forming agents (e.g. ethyl cellulose, acrylates, polymethacrylates) and/or adjuvants. Each of the above excipients represents a separate embodiment of the present invention.

In another embodiment, the pharmaceutical compositions provided herein are controlled-release compositions, i.e. compositions in which the GLP-1R antagonist is released over a period of time after administration. Controlled- or sustained-release compositions include formulation in lipophilic depots (e.g. fatty acids, waxes, oils). In another embodiment, the composition is an immediate-release composition, i.e. a composition in which all the GLP-1R antagonist is released immediately after administration.

In another embodiment, the pharmaceutical composition is delivered in a controlled release system. In another embodiment, the agent is administered using intravenous infusion, an implantable osmotic pump, a transdermal patch, liposomes, or other modes of administration. In another embodiment, a pump is used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials are used; e.g. in microspheres in or an implant. In yet another embodiment, a controlled release system is placed in proximity to the therapeutic target, thus requiring only a fraction of the systemic dose (see, e.g., Goodson, in Medical Applications of Controlled Release, supra, vol. 2, pp. 115-138 (1984); and Langer R, Science 249: 1527-1533 (1990).

The compositions also include, in another embodiment, incorporation of the active material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts.) Such compositions will influence the physical state, solubility, stability, rate of in vivo release, and rate of in vivo clearance.

Also included in the present invention are particulate compositions coated with polymers (e.g. poloxamers or poloxamines) and the compound coupled to antibodies directed against tissue-specific receptors, ligands or antigens or coupled to ligands of tissue-specific receptors.

Also comprehended by the invention are compounds modified by the covalent attachment of water-soluble polymers such as polyethylene glycol, copolymers of polyethylene glycol and polypropylene glycol, carboxymethyl cellulose, dextran, polyvinyl alcohol, polyvinylpyrrolidone or polyproline. The modified compounds are known to exhibit substantially longer half-lives in blood following intravenous injection than do the corresponding unmodified compounds (Abuchowski et al., 1981; Newmark et al., 1982; and Katre et al., 1987). Such modifications also increase, in another embodiment, the compound's solubility in aqueous solution, eliminate aggregation, enhance the physical and chemical stability of the compound, and greatly reduce the immunogenicity and reactivity of the compound. In another embodiment, the desired in vivo biological activity is achieved by the administration of such polymer-compound abducts less frequently or in lower doses than with the unmodified compound.

The preparation of pharmaceutical compositions that contain an active component, for example by mixing, granulating, or tablet-forming processes, is well understood in the art. The active therapeutic ingredient is often mixed with excipients that are pharmaceutically acceptable and compatible with the active ingredient. For oral administration, the GLP-1R antagonist or its physiologically tolerated derivatives such as salts, esters, N-oxides, and the like is mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions. For parenteral administration, the GLP-1R antagonist or its physiologically tolerated derivatives such as salts, esters, N-oxides, and the like is converted into a solution, suspension, or emulsion, if desired with the substances customary and suitable for this purpose, for example, solubilizers or other substances.

An active component is, in another embodiment, formulated into the composition as neutralized pharmaceutically acceptable salt forms. Pharmaceutically acceptable salts include the acid addition salts (formed with the free amino groups of the polypeptide or antibody molecule), which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

In another embodiment, the dose of the GLP-1R antagonist is 1 pmol/kg/min. In another embodiment, the dose is 2 pmol/kg/min. In another embodiment, the dose is 3 pmol/kg/min. In another embodiment, the dose is 5 pmol/kg/min. In another embodiment, the dose is 7 pmol/kg/min. In another embodiment, the dose is 10 pmol/kg/min. In another embodiment, the dose is 12 pmol/kg/min. In another embodiment, the dose is 15 pmol/kg/min. In another embodiment, the dose is 20 pmol/kg/min. In another embodiment, the dose is 25 pmol/kg/min. In another embodiment, the dose is 30 pmol/kg/min. In another embodiment, the dose is 50 pmol/kg/min. In another embodiment, the dose is 70 pmol/kg/min. In another embodiment, the dose is 100 pmol/kg/min. In another embodiment, the dose is 120 pmol/kg/min. In another embodiment, the dose is 150 pmol/kg/min. In another embodiment, the dose is 200 pmol/kg/min. In another embodiment, the dose is 250 pmol/kg/min. In another embodiment, the dose is 300 pmol/kg/min. In another embodiment, the dose is 400 pmol/kg/min. In another embodiment, the dose is 500 pmol/kg/min. In another embodiment, the dose is 700 pmol/kg/min. In another embodiment, the dose is 1000 pmol/kg/min. In another embodiment, the dose is 1200 pmol/kg/min. In another embodiment, the dose is 1500 pmol/kg/min. In another embodiment, the dose is more than 1500 pmol/kg/min.

In another embodiment, the dose is 30-500 pmol/kg/min. In another embodiment, the dose is 1-2 pmol/kg/min. In another embodiment, the dose is 1-3 pmol/kg/min. In another embodiment, the dose is 1-5 pmol/kg/min. In another embodiment, the dose is 1-10 pmol/kg/min. In another embodiment, the dose is 1-20 pmol/kg/min. In another embodiment, the dose is 1-40 pmol/kg/min. In another embodiment, the dose is 1-60 pmol/kg/min. In another embodiment, the dose is 1-100 pmol/kg/min. In another embodiment, the dose is 1-200 pmol/kg/min. In another embodiment, the dose is 1-300 pmol/kg/min. In another embodiment, the dose is 2-5 pmol/kg/min. In another embodiment, the dose is 2-10 pmol/kg/min. In another embodiment, the dose is 2-20 pmol/kg/min. In another embodiment, the dose is 2-40 pmol/kg/min. In another embodiment, the dose is 2-70 pmol/kg/min. In another embodiment, the dose is 2-100 pmol/kg/min. In another embodiment, the dose is 2-200 pmol/kg/min. In another embodiment, the dose is 2-300 pmol/kg/min. In another embodiment, the dose is 5-10 pmol/kg/min. In another embodiment, the dose is 5-20 pmol/kg/min. In another embodiment, the dose is 5-40 pmol/kg/min. In another embodiment, the dose is 5-70 pmol/kg/min. In another embodiment, the dose is 5-100 pmol/kg/min. In another embodiment, the dose is 5-200 pmol/kg/min. In another embodiment, the dose is 5-300 pmol/kg/min. In another embodiment, the dose is 10-20 pmol/kg/min. In another embodiment, the dose is 10-40 pmol/kg/min. In another embodiment, the dose is 10-70 pmol/kg/min. In another embodiment, the dose is 10-100 pmol/kg/min. In another embodiment, the dose is 10-150 pmol/kg/min. In another embodiment, the dose is 10-200 pmol/kg/min. In another embodiment, the dose is 10-300 pmol/kg/min. In another embodiment, the dose is 10-500 pmol/kg/min. In another embodiment, the dose is 20-40 pmol/kg/min. In another embodiment, the dose is 20-70 pmol/kg/min. In another embodiment, the dose is 20-100 pmol/kg/min. In another embodiment, the dose is 20-150 pmol/kg/min. In another embodiment, the dose is 20-200 pmol/kg/min. In another embodiment, the dose is 20-300 pmol/kg/min. In another embodiment, the dose is 20-500 pmol/kg/min. In another embodiment, the dose is 30-40 pmol/kg/min. In another embodiment, the dose is 30-70 pmol/kg/min. In another embodiment, the dose is 30-100 pmol/kg/min. In another embodiment, the dose is 30-150 pmol/kg/min. In another embodiment, the dose is 30-200 pmol/kg/min. In another embodiment, the dose is 30-300 pmol/kg/min. In another embodiment, the dose is 30-500 pmol/kg/min. In another embodiment, the dose is 50-100 pmol/kg/min. In another embodiment, the dose is 50-150 pmol/kg/min. In another embodiment, the dose is 50-200 pmol/kg/min. In another embodiment, the dose is 50-300 pmol/kg/min. In another embodiment, the dose is 50-500 pmol/kg/min. In another embodiment, the dose is 100-150 pmol/kg/min. In another embodiment, the dose is 100-200 pmol/kg/min. In another embodiment, the dose is 100-300 pmol/kg/min. In another embodiment, the dose is 100-500 pmol/kg/min. In another embodiment, the dose is 100-1000 pmol/kg/min. In another embodiment, the dose is 100-1500 pmol/kg/min.

In another embodiment, the dosage is 20 nmol/kg/day. In another embodiment, the dosage is 25 nmol/kg/day. In another embodiment, the dosage is 30 nmol/kg/day. In another embodiment, the dosage is 40 nmol/kg/day. In another embodiment, the dosage is 60 nmol/kg/day. In another embodiment, the dosage is 80 nmol/kg/day. In another embodiment, the dosage is 100 nmol/kg/day. In another embodiment, the dosage is 150 nmol/kg/day. In another embodiment, the dosage is 200 nmol/kg/day. In another embodiment, the dosage is 300 nmol/kg/day. In another embodiment, the dosage is 400 nmol/kg/day. In another embodiment, the dosage is 600 nmol/kg/day. In another embodiment, the dosage is 800 nmol/kg/day. In another embodiment, the dosage is 1000 nmol/kg/day. In another embodiment, the dosage is 1200 nmol/kg/day. In another embodiment, the dosage is 1500 nmol/kg/day. In another embodiment, the dosage is 2000 nmol/kg/day. In another embodiment, the dosage is more than 2000 nmol/kg/day.

In another embodiment, the dosage is 20-2000 nmol/kg/day. In another embodiment, the dosage is 20-700 nmol/kg/day. In another embodiment, the dosage is 20-100 nmol/kg/day. In another embodiment, the dosage is 20-200 nmol/kg/day. In another embodiment, the dosage is 20-300 nmol/kg/day. In another embodiment, the dosage is 20-500 nmol/kg/day. In another embodiment, the dosage is 20-1000 nmol/kg/day. In another embodiment, the dosage is 40-100 nmol/kg/day. In another embodiment, the dosage is 40-200 nmol/kg/day. In another embodiment, the dosage is 40-300 nmol/kg/day. In another embodiment, the dosage is 40-500 nmol/kg/day. In another embodiment, the dosage is 40-1000 nmol/kg/day. In another embodiment, the dosage is 60-100 nmol/kg/day. In another embodiment, the dosage is 60-150 nmol/kg/day. In another embodiment, the dosage is 60-200 nmol/kg/day. In another embodiment, the dosage is 60-300 nmol/kg/day. In another embodiment, the dosage is 60-500 nmol/kg/day. In another embodiment, the dosage is 60-1000 nmol/kg/day. In another embodiment, the dosage is 100-150 nmol/kg/day. In another embodiment, the dosage is 100-200 nmol/kg/day. In another embodiment, the dosage is 100-300 nmol/kg/day. In another embodiment, the dosage is 100-500 nmol/kg/day. In another embodiment, the dosage is 100-1000 nmol/kg/day. In another embodiment, the dosage is 100-1500 nmol/kg/day. In another embodiment, the dosage is 200-300 nmol/kg/day. In another embodiment, the dosage is 200-500 nmol/kg/day. In another embodiment, the dosage is 200-1000 nmol/kg/day. In another embodiment, the dosage is 200-1500 nmol/kg/day.

Each dosage and dosage range represents a separate embodiment of the present invention.

In another embodiment, the present invention provides a composition for treating post-prandial hypoglycemia, the composition comprising a GLP-1R of the present invention.

In another embodiment, the present invention provides a composition for treating congenital hyperinsulinism, the composition comprising a GLP-1R of the present invention.

In another embodiment, a peptide of the present invention is homologous to a peptide disclosed herein. The terms "homology," "homologous," etc, when in reference to any protein or peptide, refer, in one embodiment, to a percentage of amino acid (AA) residues in the candidate sequence that are identical with the residues of a corresponding native polypeptide, after aligning the sequences and introducing gaps, if necessary, to achieve the maximum percent homology, and not considering any conservative substitutions as part of the sequence identity. Methods and computer programs for the alignment are well known in the art.

Homology is, in another embodiment, determined by computer algorithm for sequence alignment, by methods well described in the art. For example, computer algorithm analysis of nucleic acid sequence homology can include the utilization of any number of software packages available, such as, for example, the BLAST, DOMAIN, BEAUTY (BLAST Enhanced Alignment Utility), GENPEPT and TREMBL packages.

In another embodiment, "homology" refers to identity to a sequence selected from SEQ ID No: 1-10 of greater than 70%. In another embodiment, "homology" refers to identity to a sequence selected from SEQ ID No: 1-10 of greater than 72%. In another embodiment, "homology" refers to identity to one of SEQ ID No: 1-10 of greater than 75%. In another embodiment, "homology" refers to identity to a sequence selected from SEQ ID No: 1-10 of greater than 78%. In another embodiment, "homology" refers to identity to one of SEQ ID No: 1-10 of greater than 80%. In another embodiment, "homology" refers to identity to one of SEQ ID No: 1-10 of greater than 82%. In another embodiment, "homology" refers to identity to a sequence selected from SEQ ID No: 1-10 of greater than 83%. In another embodiment, "homology" refers to identity to one of SEQ ID No: 1-10 of greater than 85%. In another embodiment, "homology" refers to identity to one of SEQ ID No: 1-10 of greater than 87%. In another embodiment, "homology" refers to identity to a sequence selected from SEQ ID No: 1-10 of greater than 88%. In another embodiment, "homology" refers to identity to one of SEQ ID No: 1-10 of greater than 90%. In another embodiment, "homology" refers to identity to one of SEQ ID No: 1-10 of greater than 92%. In another embodiment, "homology" refers to identity to a sequence selected from SEQ ID No: 1-10 of greater than 93%. In another embodiment, "homology" refers to identity to one of SEQ ID No: 1-10 of greater than 95%. In another embodiment, "homology" refers to identity to a sequence selected from SEQ ID No: 1-10 of greater than 96%. In another embodiment, "homology" refers to identity to one of SEQ ID No: 1-10 of greater than 97%. In another embodiment, "homology" refers to identity to one of SEQ ID No: 1-10 of greater than 98%. In another embodiment, "homology" refers to identity to one of SEQ ID No: 1-10 of greater than 99%. In another embodiment, "homology" refers to identity to one of SEQ ID No: 1-10 of 100%. Each possibility represents a separate embodiment of the present invention.

In another embodiment, homology is determined via determination of candidate sequence hybridization, methods of which are well described in the art (See, for example, "Nucleic Acid Hybridization" Hames, B. D., and Higgins S. J., Eds. (1985); Sambrook et al., 2001, Molecular Cloning, A Laboratory Manual, Cold Spring Harbor Press, N.Y.; and Ausubel et al., 1989, Current Protocols in Molecular Biology, Green Publishing Associates and Wiley Interscience, N.Y). In other embodiments, methods of hybridization are carried out under moderate to stringent conditions, to the complement of a DNA encoding a native caspase peptide. Hybridization conditions being, for example, overnight incubation at 42° C. in a solution comprising: 10-20% formamide, 5×SSC (150 mM NaCl, 15 mM trisodium citrate), 50 mM sodium phosphate (pH 7.6), 5×Denhardt's solution, 10% dextran sulfate, and 20 µg/ml denatured, sheared salmon sperm DNA.

Protein and/or peptide homology for any AA sequence listed herein is determined, in another embodiment, by methods well described in the art, including immunoblot analysis, or via computer algorithm analysis of AA sequences, utilizing any of a number of software packages available, via established methods. Some of these packages include the FASTA, BLAST, MPsrch or Scanps packages, and, in another embodiment, employ the use of the Smith and Waterman algorithms, and/or global/local or BLOCKS alignments for analysis, for example. Each method of determining homology represents a separate embodiment of the present invention.

In another embodiment of the present invention, "nucleic acids" or "nucleotide" refers to a string of at least two base-sugar-phosphate combinations. The term includes, in one embodiment, DNA and RNA. "Nucleotides" refers, in one embodiment, to the monomeric units of nucleic acid polymers. RNA is, in one embodiment, in the form of a tRNA (transfer RNA), snRNA (small nuclear RNA), rRNA (ribosomal RNA), mRNA (messenger RNA), anti-sense RNA, small inhibitory RNA (siRNA), micro RNA (miRNA) and ribozymes. The use of siRNA and miRNA has been described (Caudy A A et al, Genes & Devel 16: 2491-96 and references cited therein). DNA can be, in other embodiments, in form of plasmid DNA, viral DNA, linear DNA, or chromosomal DNA or derivatives of these groups. In addition, these forms of DNA and RNA can be single, double, triple, or quadruple stranded. The term also includes, in another embodiment, artificial nucleic acids that contain other types of backbones but the same bases. In one embodiment, the artificial nucleic acid is a PNA (peptide nucleic acid). PNA contain peptide backbones and nucleotide bases and are able to bind, in one embodiment, to both DNA and RNA molecules. In another embodiment, the nucleotide is oxetane modified. In another embodiment, the nucleotide is modified by replacement of one or more phosphodiester bonds with a phosphorothioate bond. In another embodiment, the artificial nucleic acid contains any other variant of the phosphate backbone of native nucleic acids known in the art. The use of phosphothiorate nucleic acids and PNA are known to those skilled in the art, and are described in, for example, Neilsen P E, Curr Opin Struct Biol 9:353-57; and Raz N K et al Biochem Biophys Res Commun. 297:1075-84. The production and use of nucleic acids is known to those skilled in art and is described, for example, in Molecular Cloning, (2001), Sambrook and Russell, eds. and Methods in Enzymology: Methods for molecular cloning in eukaryotic cells (2003) Purchio and G. C. Fareed. Each nucleic acid derivative represents a separate embodiment of the present invention.

In another embodiment, the present invention provides a chimeric molecule, comprising a fusion of an exendin or GLP peptide with a tag polypeptide that provides an epitope to which an anti-tag antibody can selectively bind. The epitope tag is placed, in other embodiments, at the amino- or carboxyl-terminus of the protein or in an internal location therein. The presence of such epitope-tagged forms of exendin or GLP peptides is detected, in another embodiment, using an antibody against the tag polypeptide. In another embodiment, inclusion of the epitope tag enables the exendin or GLP peptide to be readily purified by affinity purification using an anti-tag antibody or another type of affinity matrix that binds to the epitope tag. Various tag polypeptides and their respective antibodies are known in the art. Examples include poly-histidine (poly-his) or poly-histidine-glycine (poly-his-gly) tags; the flu HA tag polypeptide and its antibody 12CA5 (Field et al., Mol. Cell. Biol., 8: 2159-2165 (1988)); the c-myc tag and the 8F9, 3C7, 6E10, G4, B7 and 9E10 antibodies thereto (Evan et al., Molecular and Cellular Biology, 5: 3610-3616 (1985)); and the Herpes Simplex virus glycoprotein D (gD) tag and its antibody (Paborsky et al., Protein Engineering, 3(6): 547-553 (1990)). Other tag polypeptides include the Flag-peptide (Hopp et al., BioTechnology, 6: 1204-1210 (1988)); the KT3 epitope peptide (Martin et al., Science, 255: 192-194 (1992)); a tubulin epitope peptide (Skinner et al., J. Biol.

Chem., 266:15163-15166 (1991)); and the T7 gene 10 protein peptide tag (Lutz-Freyermuth et al., Proc. Natl. Acad. Sci. USA, 87: 6393-6397 (1990)). In another embodiment, the chimeric molecule comprises a fusion of the exendin or GLP peptide with an immunoglobulin or a particular region of an immunoglobulin. Methods for constructing fusion proteins are well known in the art, and are described, for example, in LaRochelle et al., J. Cell Biol., 139(2): 357-66 (1995); Heidaran et al., FASEB J., 9(1): 140-5 (1995); Ashkenazi et al., Int. Rev. Immunol., 10(2-3): 219-27 (1993) and Cheon et al., PNAS USA, 91(3): 989-93 (1994).

In another embodiment, the present invention provides a kit comprising a compound or composition utilized in performing a method of the present invention. In another embodiment, the present invention provides a kit comprising a composition, tool, or instrument of the present invention. Each possibility represents a separate embodiment of the present invention.

In one embodiment, the term "administering" or refers to a method of exposure, which can be direct or indirect. In one method such contact comprises direct injection of the target cell through any means well known in the art, such as microinjection. In another embodiment, supply to the cell is indirect, such as via provision in a culture medium that surrounds the cell, or administration to a subject, or via any route known in the art. In another embodiment, the term means that the GLP-1R antagonist of the present invention is introduced into a subject receiving treatment, and the compound is allowed to come in contact with the GLP-1R antagonist in vivo. Each possibility represents a separate embodiment of the present invention.

"Administering," in one embodiment, refers to directly contacting the target cell with a composition of the present invention. In another embodiment, "contacting" refers to indirectly contacting the target cell with a composition of the present invention. In another embodiment, methods of the present invention include methods in which the subject is contacted with a GLP-1R antagonist which is brought in contact with the target cell by diffusion, perfusion, infusion or any other active transport or passive transport process known in the art or later developed by which compounds circulate within the body. Each possibility represents a separate embodiment of the present invention.

In another embodiment of the methods of the present invention, the GLP-1R antagonist is carried in the subjects' bloodstream to the subject's target cell. In another embodiment, the GLP-1R antagonist is carried by diffusion to the subject's target cell. In another embodiment, the GLP-1R antagonist is carried by active transport to the subject's target cell. In another embodiment, the GLP-1R antagonist is administered to the subject in such a way that it directly contacts the subject's target cell. Each possibility represents a separate embodiment of the present invention.

The target tissue of methods and compositions of the present invention is, in another embodiment, the pancreatic islet. In another embodiment, the target tissue is the hypothalamus. In another embodiment, the target tissue is the hippocampus. In another embodiment, the target tissue is the cerebral cortex. In another embodiment, the target tissue is the kidney. In another embodiment, the target tissue is the heart. In another embodiment, the target tissue is the gastrointestinal tract. In another embodiment, the target tissue is any other target tissue known in the art that expresses a GLP-1R Each possibility represents a separate embodiment of the present invention.

In other embodiments, the present invention provides a method of treating any disease, disorder, symptom, or side effect associated with post-prandial hypoglycemia, the method comprising administering a GLP-1R antagonist of the present invention. In other embodiments, the present invention provides a method of treating any disease, disorder, symptom, or side effect associated with congenital hyperinsulinism, the method comprising administering a GLP-1R antagonist of the present invention.

"Treating" or "treatment" embraces in another embodiment, the amelioration of an existing condition. The skilled artisan would understand that treatment does not necessarily result in the complete absence or removal of symptoms. Treatment also embraces palliative effects: that is, those that reduce the likelihood of a subsequent medical condition. The alleviation of a condition that results in a more serious condition is encompassed by this term. In another embodiment, the term "treating" refers to the management and care of a patient for the purpose of combating the disease, condition, or disorder and includes the administration of of the compositions described herein to prevent the onset of the symptoms or complications, alleviating the symptoms or complications, or eliminating the disease, condition, or disorder. Treating HI, for example, may include but is not limited to lowering elevated blood glucose and stabilizing insulin levels in patients.

In another embodiment of methods and compositions of the present invention, the GLP-1R antagonist is administered in combination with a drug used to treat one of the above disorders. In another embodiment, the drug is diazoxide. In another embodiment, the drug is octreotide. In another embodiment, the drug is any other drug known in the art that can be used to treat a hyperinsulinism. In another embodiment, the drug is any other drug known in the art that can be used to treat a post-prandial hypoglycemia. Each possibility represents a separate embodiment of the present invention.

Each of the above additives, excipients, formulations and methods of administration represents a separate embodiment of the present invention.

EXPERIMENTAL DETAILS SECTION

Materials and Methods

Animals

SUR-1$^{-/-}$ mice were kindly provided by Dr. Mark A. Magnuson. The generation and genotyping of SUR-1$^{-/-}$ mice were previously described (8). Mice are maintained in a C57Bl/6 genetic background. Twelve to eighteen week SUR-1$^{-/-}$ and wild-type littermatte control mice were used in all experiments. Mice were maintained on a 12:12-h light-dark cycle and were fed a standard rodent chow diet. All procedures were approved and carried out according to the University of Pennsylvania Institutional Animal Care and Use Committee guidelines.

Exendin-(9-39) Administration

Alzet mini-osmotic pumps (model 2002; Alza, Palo Alto, Calif.) were implanted subcutaneously to deliver exendin-(9-39) (Bachem Bioscience, King of Prussia, Pa.) at a rate of 150 pmol/kg/min or vehicle (0.9% NaCl/1% BSA) for 2 weeks.

Glucose Homeostasis

For determination of fasting blood glucose levels mice were fasted for 12-16 hours. Oral glucose tolerance testing was carried after a 12-16 hour fast by administering 2 g/kg of dextrose by oral gavage (feeding needles; Popper and Sons, Inc., Hyde Park, N.Y.). For insulin tolerance testing mice received 0.5 units/kg of insulin intraperitoneally after a 4 hour fast. Blood glucose levels were measured using a hand-held glucose meter (FreeStyle; TheraSense, Alameda, Calif.). Insulin and glucagon were measured by ELISA (Mouse Endocrine Immunoassay Panel; Linco Research, Inc., St. Charles, Mo.).

Islet Studies

Islets were isolated by collagenase digestion and cultured for 3 days in RPMI 1640 medium containing 10 mM glucose. The culture medium was supplemented with 10% fetal bovine serum, 2 mM glutamine, 100 units/mL penicillin, and 50 µg/mL streptomycin. Islets were incubated at 37° C. in a 5% CO2, 95% air-humidified incubator. Batches of 100 cultured mouse islets were loaded onto a nylon filter in a chamber and perifused with Krebs-Ringer bicarbonate buffer (115 mM NaCl, 24 mM NaHCO$_3$, 5 mM KCl, 1 mM MgCl2, 2.5 mM CaCl2), 10 mM HEPES, pH 7.4) with 0.25% bovine serum albumin at a flow rate of 2 mL/min. Perifusate solutions were gassed with 95% 02, 5% CO2 and maintained at 37° C. Islets were stimulated with a ramp of amino acids. The physiologic mixture of 19 amino acids when used at a maximum concentration of 12 mM (about 3 times physiological concentration) had the following composition (in mM): glutamine 2, alanine 1.25, arginine 0.53, aspartate 0.11, citrulline 0.27, glutamate 0.35, glycine 0.85, histidine 0.22, isoleucine 0.27, leucine 0.46, lysine 1.06, methionine 0.14, ornithine 0.20, phenylalanine 0.23, proline 1, serine 1.62, threonine 0.77, tryptophan 0.21, valine 0.57. Samples were collected every minute for insulin assays. Insulin was measured by radioimmunoassay (Linco Research Inc., St. Charles, Mo.).

cAMP Content Determination

Islets were isolated as above, hand-picked and cultured for three days. Cultured islets were preincubated in glucose free Krebs-Ringer bicarbonate buffer for 60 min, 100 nM exendin-(9-39) was added 30 min into the preincubation period. Then, islets were exposed to different treatments for an additional 30 min in the presence of 0.1 mM isobutylmethylzanthine (IBMX). After incubation, islets were washed 2 times by cold glucose-free Hank's buffer. cAMP was measured in islet lysates by ELISA (GE/Amersham Biosciences, Piscataway, N.J.).

Cytosolic Free Ca2+ Measurements

Mouse islets were isolated and cultured on poly-Llysine coated glass coverslips under the same conditions as described above. The perifusion procedure and cytosolic-free Ca2+([Ca2+]i) measurement were described previously (24). In brief, the coverslip with attached islets was incubated with 15 µM Fura-2 acetoxymethylester (Molecular Probes, Eugene, Oreg.) in Krebs-Ringer bicarbonate buffer with 5 mM glucose for 35 min at 37° C. Islets were then perifused with Krebs-Ringer bicarbonate buffer with 0.25% bovine serum albumin at 37° C. at a flow rate of 2 mL/min, while various agents were applied. [Ca2+]i was measured with a dual wavelength fluorescence microscope as previously described.

Statistical Evaluation

Data presented are mean±SEM and compared using student's t test. For glucose and insulin tolerance testing, values were compared by repeated-measures ANOVA. Differences were considered significant at p<0.05.

Figure 1B:
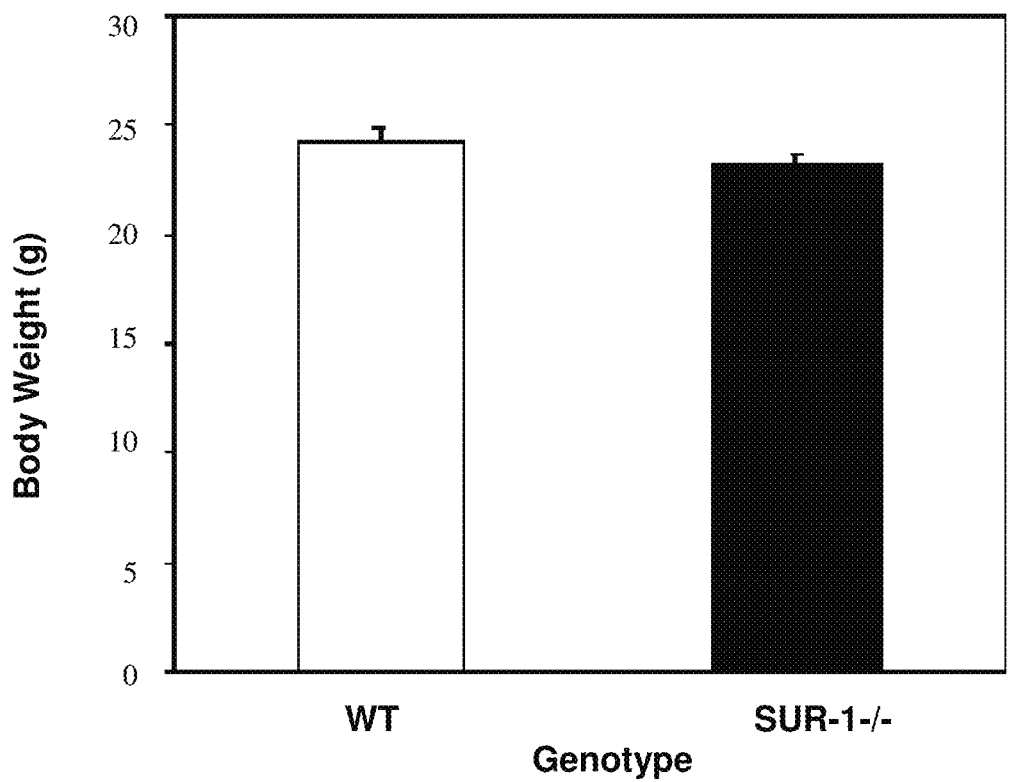
Figure 1C:
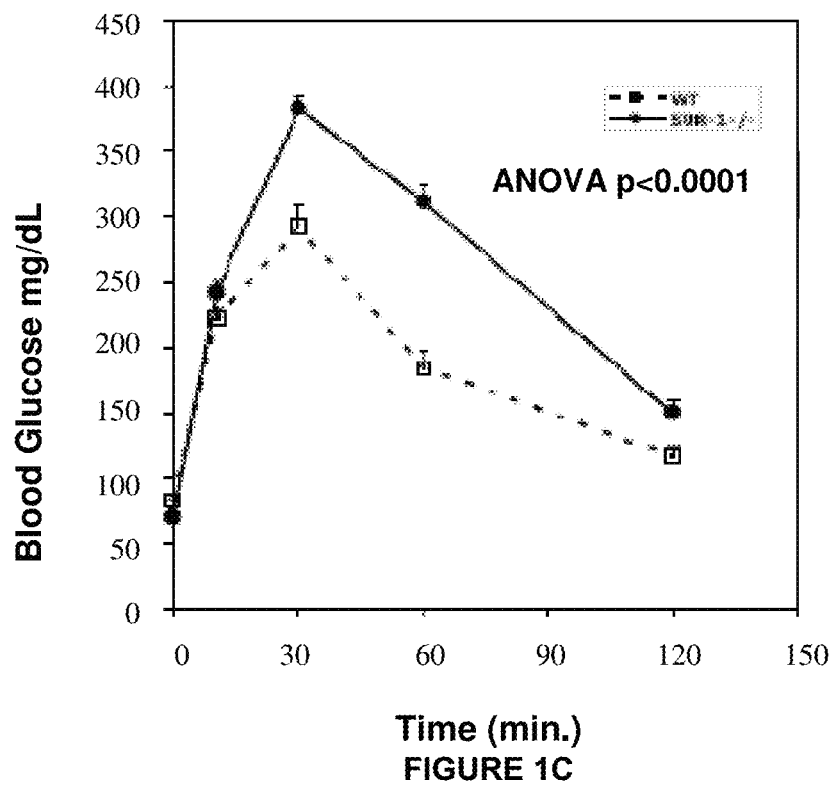
Figure 1D:
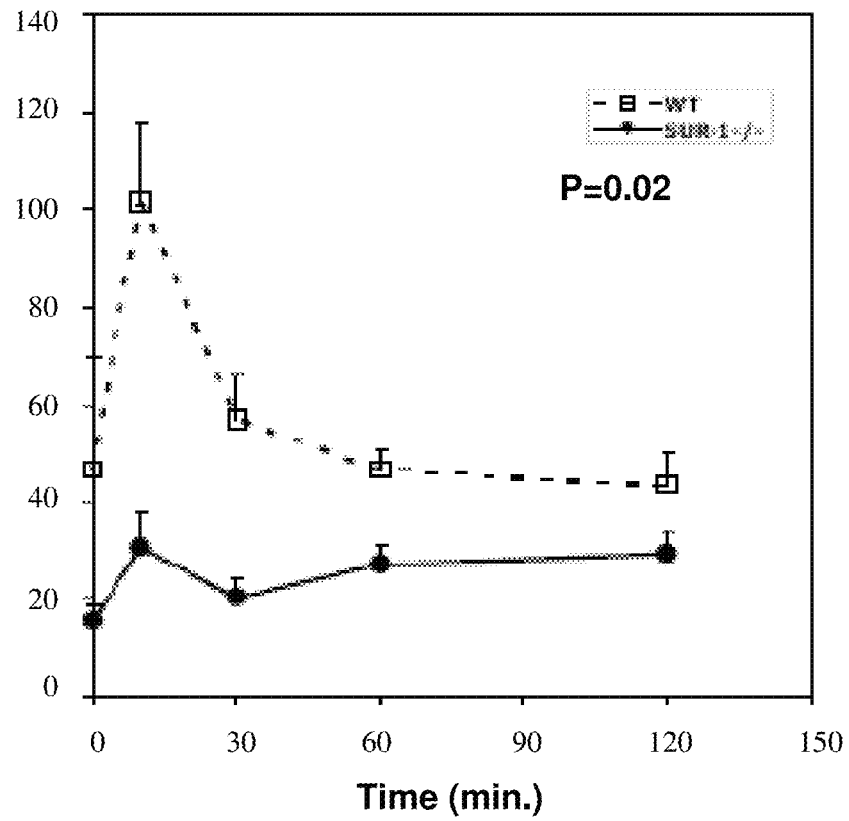

Example 1: Exendin-(9-39) Significantly Raises Fasting Blood Glucose Levels in SUR-1–/– Mice Twelve-18 week old male SUR-1$^{-/-}$ and wildtype littermates underwent a baseline evaluation including fasting blood glucose measurements and oral glucose tolerance testing, followed by randomization to treatment with exendin-(9-39) (150 pmol/kg/min) or vehicle (0.9% NaCl, 1% BSA). Fasting blood glucose levels were determined after an overnight fast on days 3 and 7 of the infusion. In addition, oral glucose tolerance and insulin sensitivity were evaluated during treatment. Fasting blood glucose levels were significantly lower in SUR-1$^{-/-}$ mice compared to wild-type littermates (59.4±1.5 mg/dL vs. 75±1.8 mg/dL, p=0.00000003) (FIG. 1A), while body weight was not different (FIG. 1B). After an oral load of glucose, SUR-1$^{-/-}$ mice were glucose intolerant when compared to littermate wild-type controls (p<0.0001, repeated measures ANOVA) (FIG. 1C). The SUR-1' mice have a significant impairment of insulin secretion in response to an oral glucose load (wildtype vs. SUR-1$^{-/-}$: p=0.02, repeated measures ANOVA) (FIG. 1D). Exendin-(9-39) was administered via an Azlet miniosmotic subcutaneous pump at a continuous infusion rate of 150 pmol/kg/min for 2 weeks. This dose was chosen based on results of a pilot study evaluating different doses previously shown to have an effect in normal humans and mice.

Figure 2:
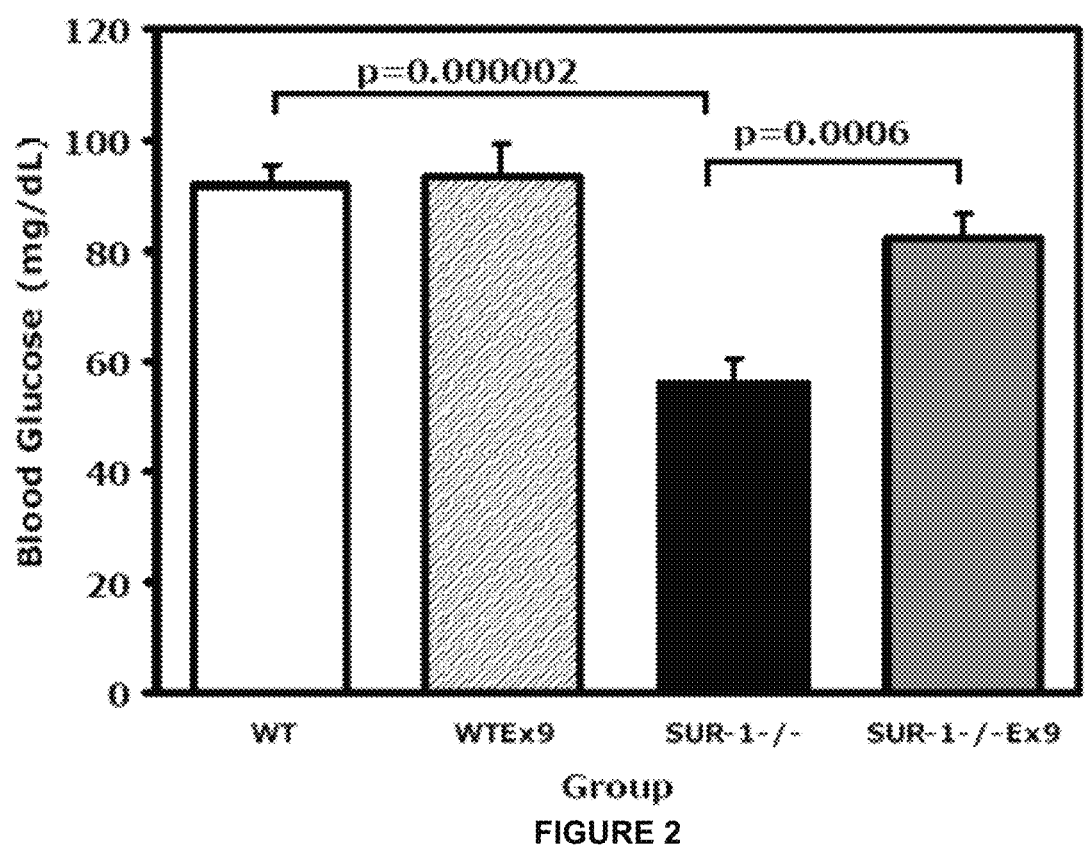
FIG. 2 shows exendin-(9-39) normalized fasting blood glucose levels in SUR-1$^{-/-}$ mice. Blood glucose levels were determined after a 12-16 hour fast on day 7. Vehicle-treated wild-type littermates (n=13) (white bar); exendin-(9-39) treated wild-type littermates (n=10) (hatched bar); vehicle-treated SUR-1$^{-/-}$ mice (n=11) (black bar); exendin-(9-39) treated SUR-1$^{-/-}$ mice (n=11) (gray bar)

On day 7, fasting blood glucose was significantly lower in vehicle-treated SUR-1$^{-/-}$ mice compared to vehicle-treated wild-type littermates (p=0.000002) (FIG. 2). Treatment with exendin-(9-39) significantly raised fasting blood glucose levels in SUR-1$^{-/-}$ mice compared to vehicle treated vehicle treated SUR-1$^{-/-}$ mice (82.2±6.3 mg/dL vs. 63.2±4.9 mg/dL, p=0.03, on day 3; 82±4.7 mg/dL vs. 56.4±4.3 mg/dL, p=0.0006, on day 7). Fasting blood glucose levels were not different in exendin-(9-39)-treated wild-type mice compared to vehicle-treated wild type controls, in contrast to our previous observations in wild-type BALB/c mice, suggesting a strain specific role of the GLP-1 receptor in fasting glycemia. Exendin-(9-39) did not impact weight gain in SUR-1$^{-/-}$ nor wildtype littermate controls.

Example 2: Extendin-(9-39) Directly Affects Islet Insulin Secretion

Figure 3A:
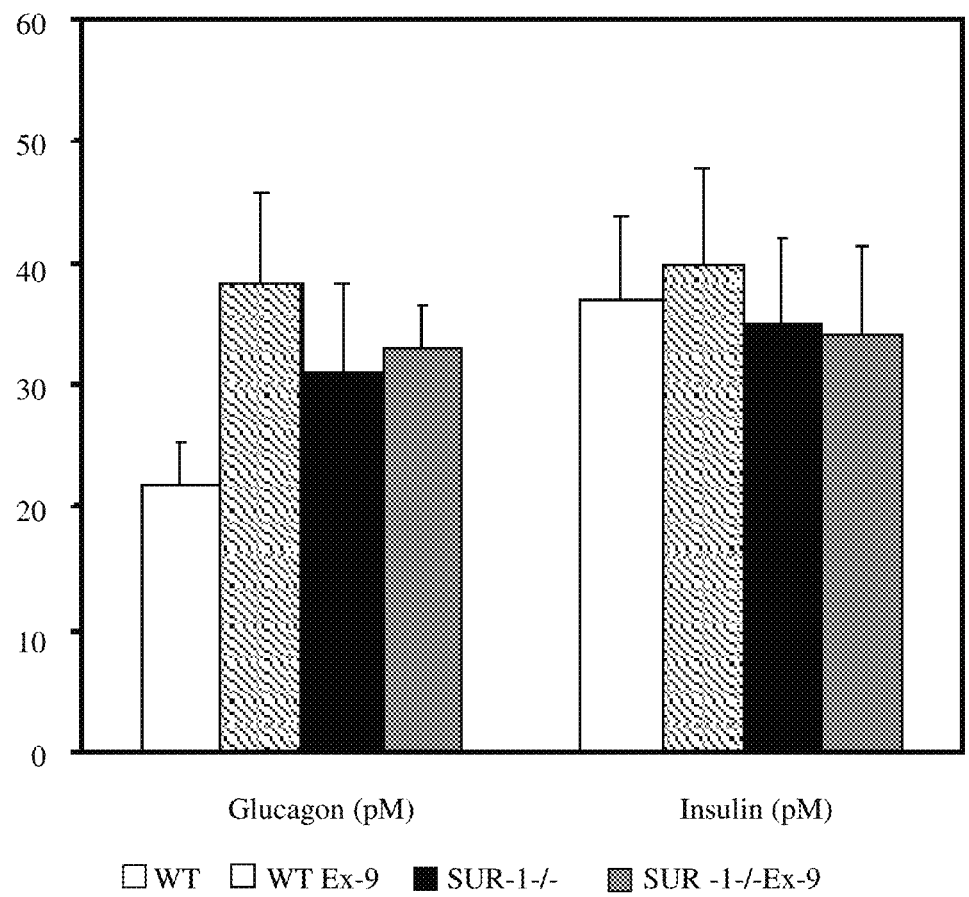
FIGS. 3A-3B show fasting hormonal profile.
Figure 3B:
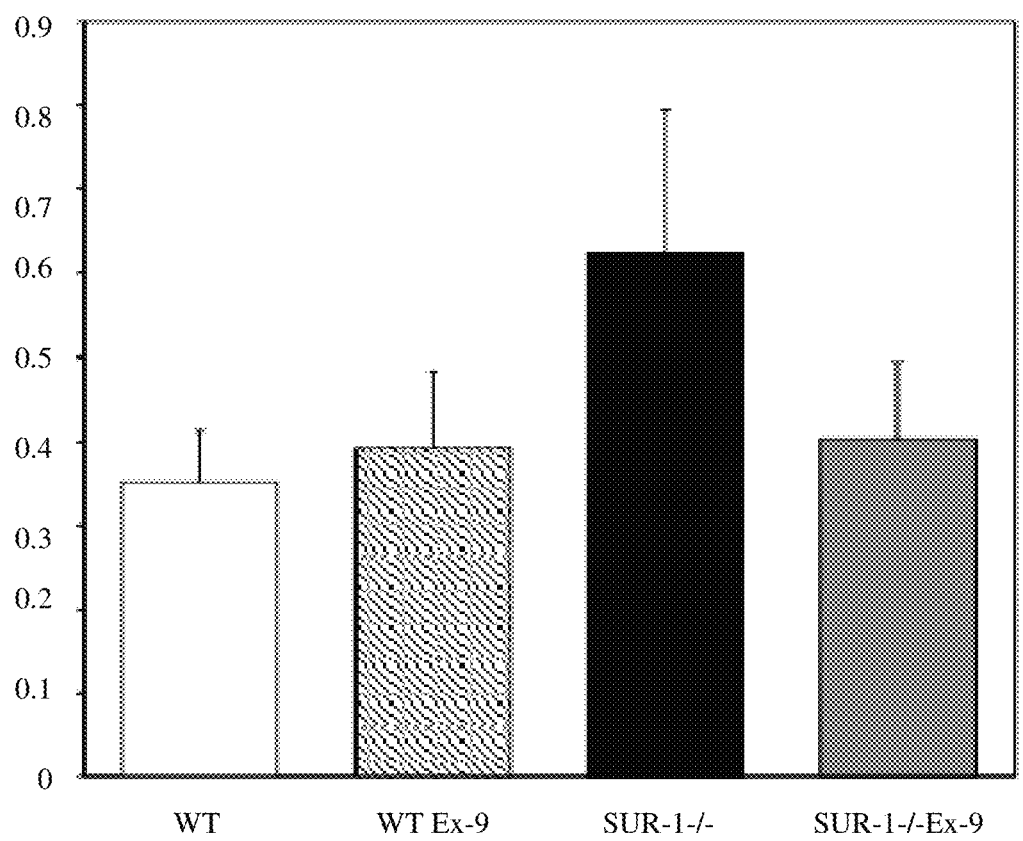

During treatment, fasting insulin and glucagon levels were not different among the treatment groups (FIG. 3A); however in the setting of lower fasting blood glucose levels insulin levels were inappropriately elevated in vehicle treated SUR-1$^{-/-}$ mice and glucagon levels failed to rise as expected in response to the hypoglycemia. Insulin/glucose ratio is increased in SUR-1$^{-/-}$ mice compared to wild-type littermate controls mice FIG. 3B) (WT vs. SUR-1: p=0.04) and is normalized by exendin-(9-39) treatment (WT vs. SUR-1$^{-/-}$ Ex-(9-39): p=0.32), suggestive of a direct islet effect of exendin-(9-39) on insulin secretion.

Figure 5:
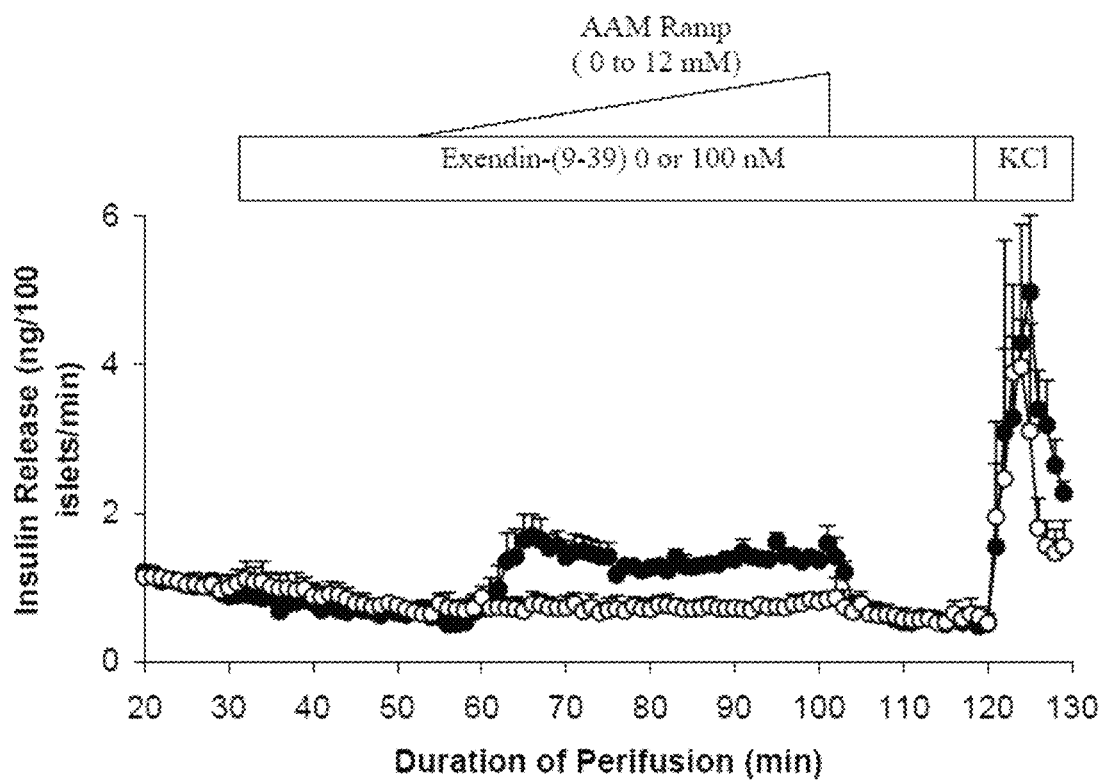
FIG. 5 shows the Effect of exendin-(9-39) on fuel responsiveness of SUR-1$^{-/-}$ islets. Isolated islets from SUR-1$^{-/-}$ mice were cultured for 3 days in RPMI 1640 medium containing 10 mM glucose. Batches of 100 cultured islets were perifused with a ramp of a physiologic mixture of amino acids (0-12 mM) in the presence (open circles) or absence (black circles) of exendin-(9-39) at a concentration of 100 nM. Results are presented as means±S.E. for 100 islets from 3 separate perifusions for each condition.

Given the observed in vivo effects on insulin secretion but not insulin sensitivity, it was next determined whether exendin-(9-39) exerts a direct effect on SUR-1$^{-/-}$ islet function. Examination was made of the effect of exendin-(9-39) on the abnormal response of SUR-1$^{-/-}$ islets to fuel induced insulin secretion (specifically, the hyper responsiveness to amino acids). Isolated islets were perfused with a mixture of amino acids. SUR-1$^{-/-}$ islets abnormally released insulin in response to ramp stimulation by a physiologic mixture of 19 amino acids (using an increment of 0.04 mM/min for glutamine and 0.2 mM/min for the other amino acids). This response to amino acids was blocked by exendin-(9-39) (FIG. 5). The insulin response to KCl was similar in the presence and absence of exendin-(9-39).

Figure 4A:
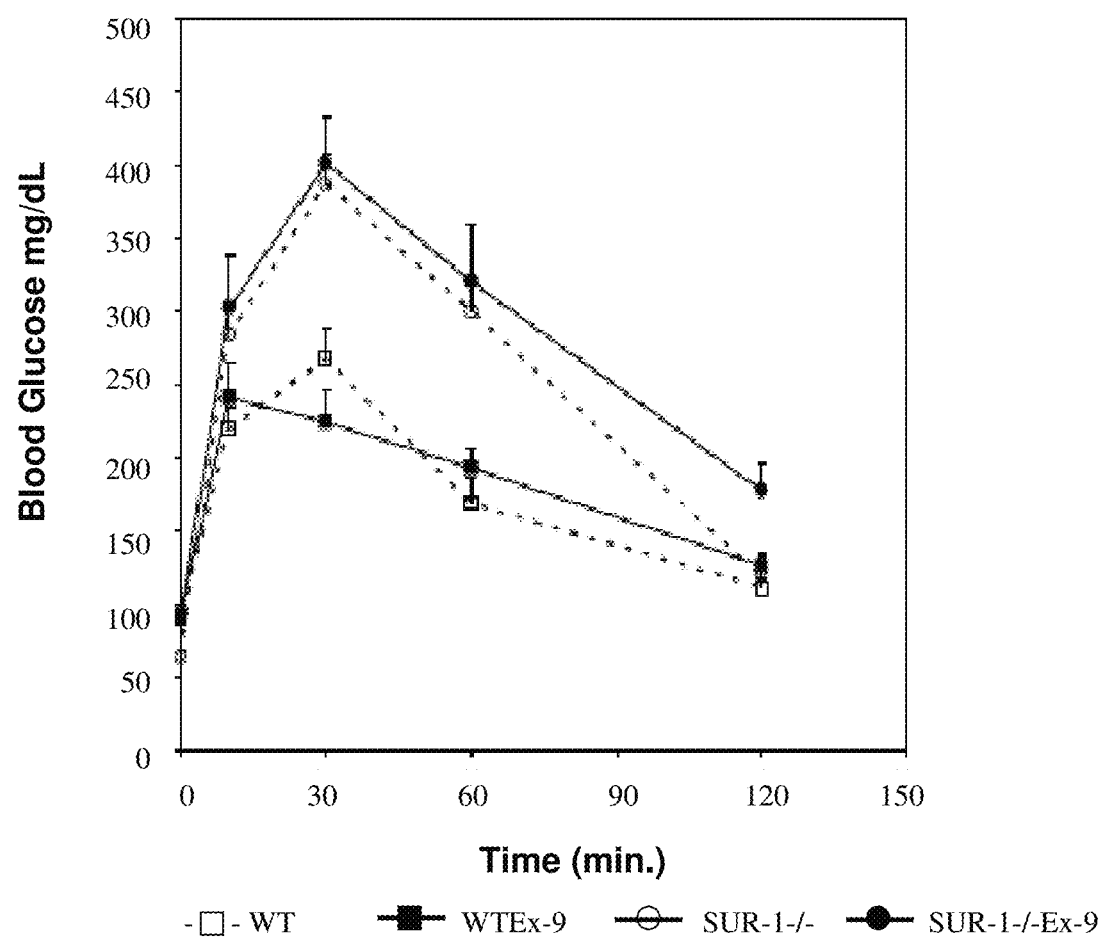
FIGS. 4A-4B. exendin-(9-39) did not influence glucose tolerance or insulin sensitivity.

Example 3: Exendin-(9-39) does not Impair Glucose Tolerance or Insulin Sensitivity in SUR-1$^{-/-}$-Mice Despite the marked effect on fasting blood glucose levels, treatment with exendin-(9-39) did not significantly impair glucose tolerance in SUR-1$^{-/-}$ mice, except for a minor delay in the return to baseline blood glucose levels at the 120 minute time point. Similarly, there was no effect on glucose tolerance in wild-type littermates during treatment with exendin-(9-39) (FIG. 4A).

Figure 4B:
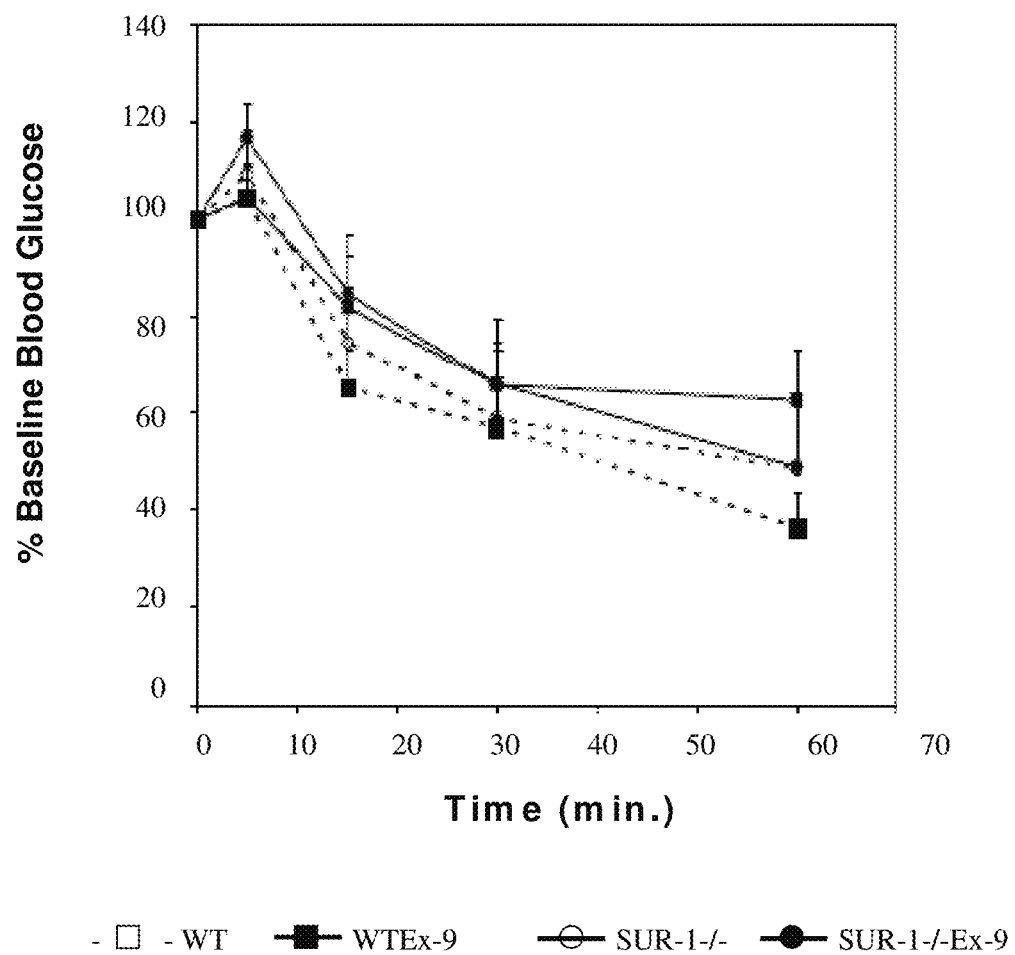

To determine the mechanism of action for the effect of exendin-(9-39) on fasting blood glucose levels insulin sensitivity was assessed by an insulin tolerance test. Insulin sensitivity was not different between SUR-1$^{-/-}$ and wild-type littermates and exendin-(9-39) did not impact peripheral insulin sensitivity in any of the treatment groups (FIG. 4B).

Example 4: Exendin-(9-39) Effects on Insulin Secretion in SUR-1-/- Islets are Mediated by Changes in cAMP The effect of exendin-(9-39) on cAMP was determined in static incubations of isolated islets. In the absence of exogenous GLP-1, exendin-(9-39) significantly decreased basal intracellular cAMP in SUR-1$^{-/-}$ islets (40.1±4.2 vs. 20.5±2.3 pmol/100 islets, $p<0.05$) (Table 1). The amino acid-stimulated increase in cAMP was similarly reduced by exendin-(9-39) (52.5±9.4 vs. 20.9±4.4 pmol/100 islets, $p<0.05$). In these static incubations, the effect of exendin-(9-39) on cAMP levels mirrored the effect on insulin secretion, suggesting that exendin-(9-39) effects on insulin secretion in SUR-1$^{-/-}$ islets are mediated by changes in cAMP. Baseline insulin secretion was significantly reduced by exendin-(9-39) (221±22 vs. 126±12 ng/100 islets/30 min, $p<0.05$). Similarly, exendin-(9-39) significantly reduced amino acid-stimulated insulin secretion (389±17 vs. 219±14 ng/100 islets/30 min, $p<0.01$).

TABLE 1

Exendin-(9-39) reduces baseline and stimulated cytosolic cAMP content and insulin release in SUR-1-/- islets

| Condition | cAMP Content (pmol/100 islets) | Insulin Secretion (ng/100 islets/30 min) |
| --- | --- | --- |
| Baseline | 40.1 ± 4.2 | 221 ± 22 |
| 100 nM Exendin-(9-39) | 20.5 ± 2.3 [a] | 126 ± 12 [a] |
| 4 mM AAM | 20.9 ± 4.4 [a] | 389 ± 17 [b,d] |
| 100 nM Exendin-(9-39)/ 4 mM AAM | 52.5 ± 9.4 [c] | 219 ± 14 |

Isolated SUR-1$^{-/-}$ mouse islets were cultured in 10 mM glucose for 3 days. Islets were preincubated in glucose free KRBB for 60 min. 100 nM Exendin-(9-39) was added after 30 min preincubation. Then islets were exposed to different treatment conditions for an additional 30 min. Compared with baseline condition,
[a] $p < 0.05$,
[b] $p < 0.01$. Compared with 100 nM Exendin-9/4 mM AAM,
[c] $p < 0.05$,
[d] $p < 0.01$.

Example 5: Exendin-(9-39) Effect on Insulin Secretion is Calcium-Independent

Figure 6:
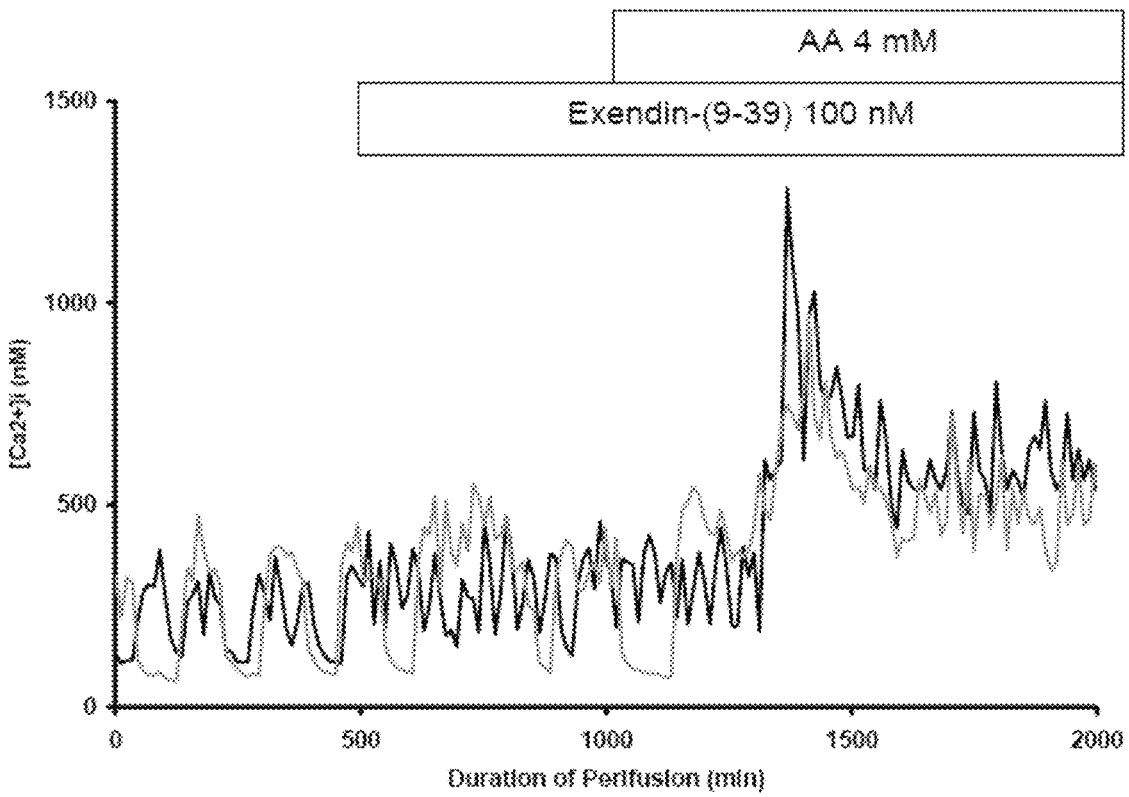
FIG. 6 shows that exendin-(9-39) did not impact $[Ca^{2+}]_i$ in SUR-1$^{-/-}$ islets. Isolated SUR-1$^{-/-}$ mouse islets were cultured with 10 mM glucose for 3 days on coverslips. $[Ca^{2+}]_i$ was continuously measured by Fura-2 fluorescence in response to amino acids (4 mM) in the presence (gray line) or absence of exendin-(9-39) (black line). Representative experiments are shown. All studies were repeated at least 3 times and showed comparable results.

The effect of exendin-(9-39) on the characteristically elevated intracellular calcium concentration of SUR-1$^{-/-}$ islets was studied. Exendin-(9-39) did not affect basal intracellular calcium (FIG. 6). As previously reported, amino acids caused a transient further rise in intracellular calcium. Exendin-(9-39) had no effect on the amino acid-stimulated rise in intracellular calcium, indicating that its effect on insulin secretion is calcium-independent.

Example 6: Exendin-(9-39) is Effective in Regulating Insulin and Plasma Glucose Levels in HI Patients After an overnight fast, subject received an intravenous infusion of 0.9% NaCl for 60 min followed by a 6 hour intravenous infusion of exendin-(9-39) at ascending doses every 120 min (100 pmol/kg/min for 120 min, then 300 pmol/kg/min for 120 min and then 500 pmol/kg/min for 120 min). On the second day, 0.9% NaCl was infused intravenously after an overnight fast for a total of 7 hours.

Figure 8:
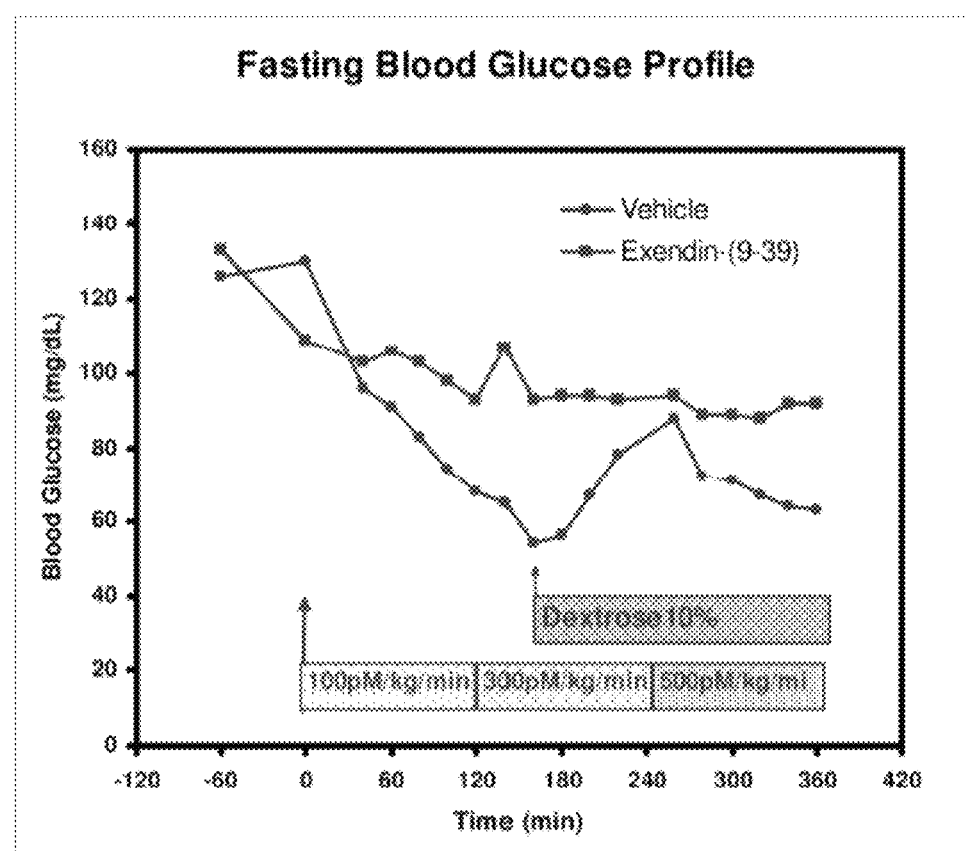
FIGS. 8 and 9 show the effect of exendin-(9-39) on fasting blood glucose (FIG. 8) and plasma insulin levels (FIG. 9) in a subject with congenital hyperinsulinism due to a mutation in ABCC8 the gene encoding the SUR-1 component of the KATP channel.
Figure 9:
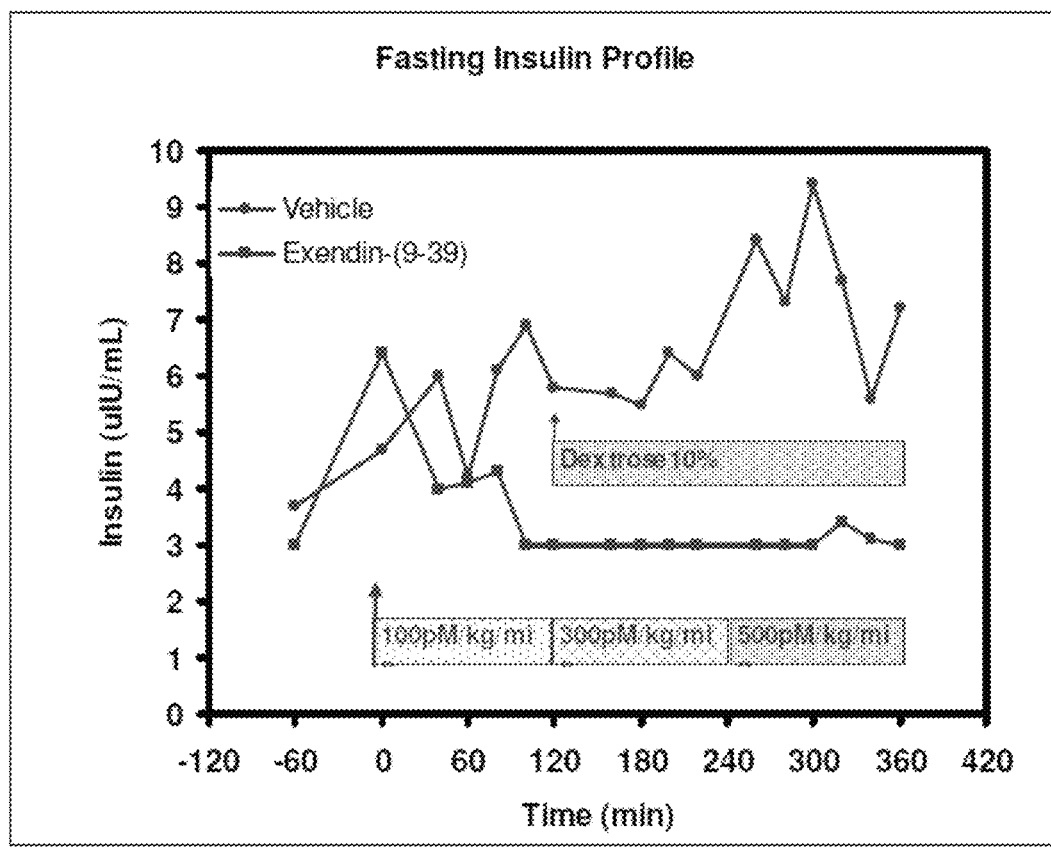

Blood samples for glucose, insulin, C-peptide, glucagon and GLP-1 were obtained at different intervals during the infusions. FIGS. 8 and 9 show the effect of exendin-(9-39) on fasting blood glucose (FIG. 8) and plasma insulin levels (FIG. 9) in a subject with congenital hyperinsulinism due to a mutation in ABCC8 the gene encoding the SUR-1 component of the KATP channel, demonstrating that exendin-(9-39) suppressed insulin suppression and prevented fasting hypoglycemia.

During the exendin-(9-39) infusion, blood glucose levels remained stable above 80 mg/dL while during the saline infusion blood glucose dropped below 60 mg/dL requiring an infusion of dextrose to normalize blood glucose. Another 2 human subject showed results indicating that exendin-(9-39) causes an elevation of fasting blood glucose levels.

Having described preferred embodiments of the invention with reference to the accompanying drawings and examples, it is to be understood that the invention is not limited to the precise embodiments, and that various changes and modifications may be effected therein by those skilled in the art without departing from the scope or spirit of the invention as defined in the appended claims.

What is claimed is:

1. A method of treating congenital hyperinsulinism in a subject having congenital hyperinsulinism comprising administering to the subject an effective amount of a peptide comprising an amino acid sequence having at least 95% identity to SEQ ID NO:1.

2. The method of claim 1, wherein the peptide is administered intravenously, parenterally, orally, intraperitoneally, subcutaneously, or by a combination thereof.

3. The method of claim 1, wherein the peptide is administered subcutaneously.

4. The method of claim 1, wherein the peptide is administered intravenously.

5. The method of claim 1, wherein the peptide is administered by infusion.

6. The method of claim 1, wherein the peptide is administered using a pump.

7. The method of claim 1, wherein the congenital hyperinsulinism is associated with a genetic abnormality or mutation.

8. The method of claim 7, wherein the genetic abnormality is associated with a mutation in a gene selected from the group consisting of a gene encoding a sulfonylurea receptor (SUR-1), a gene encoding glucokinase (GCK), a gene encoding glutamate dehydrogenase (GLUD-1), and a gene encoding mitochondrial enzyme short-chain 3-hydroxyacyl-CoA dehydrogenase (HADHSC).

9. The method of claim 1, wherein the subject has congenital hyperinsulinism, and wherein the subject is over 10 years of age.

10. The method of claim 9, wherein the subject is over 30 years of age.

11. The method of claim 1, wherein the peptide is administered to a subject from 2 years to 10 years of age.

* * * * *

UNITED STATES PATENT AND TRADEMARK OFFICE
CERTIFICATE OF CORRECTION

PATENT NO. : 10,987,407 B2
APPLICATION NO. : 16/258686
DATED : April 27, 2021
INVENTOR(S) : Doris Stoffers et al.

It is certified that error appears in the above-identified patent and that said Letters Patent is hereby corrected as shown below:

In the Specification

Please replace Lines 20-23 in Column 1 with the following:
This invention was made with government support under grant number 1K23DK073663-01 awarded by the National Institutes of Health. The government has certain rights in the invention.

Signed and Sealed this
Twenty-seventh Day of July, 2021

Drew Hirshfeld
*Performing the Functions and Duties of the*
*Under Secretary of Commerce for Intellectual Property and*
*Director of the United States Patent and Trademark Office*

SEQUENCE LISTING

<160> NUMBER OF SEQ ID NOS: 10

<210> SEQ ID NO 1
<211> LENGTH: 31

```
<212> TYPE: PRT
<213> ORGANISM: Heloderma suspectum
<220> FEATURE:
<221> NAME/KEY: MOD_RES
<222> LOCATION: (31)..(31)
<223> OTHER INFORMATION: AMIDATION

<400> SEQUENCE: 1

Asp Leu Ser Lys Gln Met Glu Glu Ala Val Arg Leu Phe Ile Glu
1               5                   10                  15

Trp Leu Lys Asn Gly Gly Pro Ser Ser Gly Ala Pro Pro Pro Ser
            20                  25                  30

<210> SEQ ID NO 2
<211> LENGTH: 87
<212> TYPE: PRT
<213> ORGANISM: MURINE

<400> SEQUENCE: 2

Met Lys Ile Ile Leu Trp Leu Cys Val Phe Gly Leu Phe Leu Ala Thr
1               5                   10                  15

Leu Phe Pro Val Ser Trp Gln Met Pro Val Glu Ser Gly Leu Ser Ser
            20                  25                  30

Glu Asp Ser Ala Ser Ser Glu Ser Phe Ala Ser Lys Ile Lys Arg His
        35                  40                  45

Ser Asp Gly Thr Phe Thr Ser Asp Leu Ser Lys Gln Met Glu Glu Glu
    50                  55                  60

Ala Val Arg Leu Phe Ile Glu Trp Leu Lys Asn Gly Gly Pro Ser Ser
65                  70                  75                  80

Gly Ala Pro Pro Pro Ser Gly
                85

<210> SEQ ID NO 3
<211> LENGTH: 38
<212> TYPE: PRT
<213> ORGANISM: MURINE

<400> SEQUENCE: 3

Gly Glu Gly Thr Phe Thr Ser Gln Leu Ser Lys Gln Met Glu Glu Glu
1               5                   10                  15

Ala Val Arg Leu Phe Ile Glu Trp Leu Lys Asn Gly Gly Pro Ser Ser
            20                  25                  30

Gly Ala Pro Pro Pro Ser
        35

<210> SEQ ID NO 4
<211> LENGTH: 41
<212> TYPE: PRT
<213> ORGANISM: MURINE

<400> SEQUENCE: 4

Lys Arg His Ser Asp Gly Thr Phe Thr Ser Asp Leu Ser Lys Gln Met
1               5                   10                  15

Glu Glu Glu Ala Val Arg Leu Phe Ile Glu Trp Leu Lys Asn Gly Gly
            20                  25                  30

Pro Ser Ser Gly Ala Pro Pro Pro Ser
        35                  40

<210> SEQ ID NO 5
<211> LENGTH: 30
<212> TYPE: PRT
```

<210> ORGANISM: MURINE

<400> SEQUENCE: 5

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 6
<211> LENGTH: 30
<212> TYPE: PRT
<213> ORGANISM: MURINE

<400> SEQUENCE: 6

His Ala Glu Gly Thr Phe Thr Ser Lys Val Ser Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 7
<211> LENGTH: 39
<212> TYPE: PRT
<213> ORGANISM: Heloderma suspectum

<400> SEQUENCE: 7

His Gly Glu Gly Thr Phe Thr Ser Asp Leu Ser Lys Gln Met Glu Glu
1               5                   10                  15
Glu Ala Val Arg Leu Phe Ile Glu Trp Leu Lys Asn Gly Gly Pro Ser
            20                  25                  30
Ser Gly Ala Pro Pro Pro Ser
        35

<210> SEQ ID NO 8
<211> LENGTH: 38
<212> TYPE: PRT
<213> ORGANISM: MURINE

<400> SEQUENCE: 8

Gly Glu Gly Thr Phe Thr Ser Glu Leu Ser Lys Gln Met Glu Glu Glu
1               5                   10                  15
Ala Val Arg Leu Phe Ile Glu Trp Leu Lys Asn Gly Gly Pro Ser Ser
            20                  25                  30
Gly Ala Pro Pro Pro Ser
        35

<210> SEQ ID NO 9
<211> LENGTH: 30
<212> TYPE: PRT
<213> ORGANISM: MURINE

<400> SEQUENCE: 9

His Ala Glu Gly Thr Phe Thr Ser Asp Val Ser Ser Tyr Leu Glu Gly
1               5                   10                  15
Gln Ala Ala Lys Glu Phe Ile Ala Trp Leu Val Lys Gly Arg
            20                  25                  30

<210> SEQ ID NO 10
<211> LENGTH: 39
<212> TYPE: PRT
<213> ORGANISM: Heloderma horridum
<220> FEATURE:
<221> NAME/KEY: MOD_RES

```
<222> LOCATION: (39)..(39)
<223> OTHER INFORMATION: AMIDATION

<400> SEQUENCE: 10

His Ser Asp Gly Thr Phe Thr Ser Asp Leu Ser Lys Gly Met Glu Glu
1               5                   10                  15
Glu Ala Val Arg Leu Phe Ile Glu Trp Leu Lys Asn Gly Gly Pro Ser
            20                  25                  30
Ser Gly Ala Pro Pro Pro Ser
            35
```